(12) United States Patent
Vincent

(10) Patent No.: US 9,188,587 B2
(45) Date of Patent: Nov. 17, 2015

(54) NEUROLOGICAL AUTOIMMUNE DISORDERS

(75) Inventor: Angela Vincent, Oxford (GB)

(73) Assignee: ISIS INNOVATION LIMITED, Oxford (GB)

(*) Notice: Subject to any disclaimer, the term of this patent is extended or adjusted under 35 U.S.C. 154(b) by 114 days.

(21) Appl. No.: 13/125,796

(22) PCT Filed: Oct. 26, 2009

(86) PCT No.: PCT/GB2009/051441
§ 371 (c)(1),
(2), (4) Date: Aug. 16, 2011

(87) PCT Pub. No.: WO2010/046716
PCT Pub. Date: Apr. 29, 2010

(65) Prior Publication Data
US 2012/0114666 A1 May 10, 2012

(30) Foreign Application Priority Data
Oct. 25, 2008 (GB) .................................. 0819634.7

(51) Int. Cl.
*G01N 33/564* (2006.01)
*G01N 33/566* (2006.01)
*G01N 33/68* (2006.01)

(52) U.S. Cl.
CPC ............ *G01N 33/564* (2013.01); *G01N 33/566* (2013.01); *G01N 33/6896* (2013.01)

(58) Field of Classification Search
CPC . G01N 33/566; G01N 33/567; G01N 33/564; G01N 33/6893; G01N 33/6896
See application file for complete search history.

(56) References Cited

U.S. PATENT DOCUMENTS

2002/0098546 A1* 7/2002 Weber et al. .................. 435/69.1

FOREIGN PATENT DOCUMENTS

WO    WO 2010/046716    4/2010

OTHER PUBLICATIONS

Klein CJ et al. (Feb. 2013) Insights from LGI1 and CASPR2 potassium channel complex autoantibody subtyping. JAMA Neurol. 70(2):229-234. (abstract only).*
Irani, SR et al. (2010) Antibodies to Kv1 potassium channel-complex proteins leucine-rich, glioma inactivated 1 protein and contactin-associated protein-2 in limbic encephalitis, Morvan's syndrome and acquired neuromyotonia. Brain, 133:2734-2748.*
Lai M et al. (2010) Investigation of LGI1 as the antigen in limbic encephalitis previously attributed to potassium channels: a case series. Lancet Neurol. 9:776-785.*
Anti-Caspr2 rabbit polyclonal antibody product sheet, Product No. C 8737, Sigma, 2003.*
Ances, et al., "Treatment-Responsive Limbic Encephalitis Identified by Neuropil Antibodies: MRI and PET Correlates." Brain. Aug. 2005;128(Pt 8):1764-77.
Buckley, et al., "Potassium Channel Antibodies in Two Patients with Reversible Limbic Encephalitis," Ann Neurol. Jul. 2001; 50(1): 73-8.
Fukata, et al., "Epilepsy-Related Ligand/Receptor Complex LGI1 and ADAM22 Regulate Synaptic Transmission." Science. Sep. 22, 2006;313(5794):1792-5.
Hart, et al., "Autoantibodies detected to Expressed K+ Channels are Implicated in Neuromyotonia," Annals of Neurology. Feb. 1997; 41(2):238-46.
Hinson, et al., "Pathogenic Potential of IgG Binding to Water Channel Extracellular Domain in Neuromyelitis Optica." Neurology. Dec. 11, 2007; 69(24):2221-31.
Kalachikov, et al., "Mutations in LGI1 Cause Autosomal-Dominant Parial Epilepsy with Auditory Features." Nat. Genet. Mar. 2002;30(3):335-41.
Kim, et al., "Clustering of Shaker-Type K+ Channels by Ineraction with a Family of Membrane-Associated Guanylate Kinases." Nature. Nov. 2, 1995;378(6552):85-8.
Kleopa, et al., "Neuromyotonia and Limbic Encephalitis Sera Terget Mature Shaker-Type K+ Channels: Subunit Specificity Correlates with Clinical Manifestations." Brain. Jun. 2006; 129(Pt 6): 1570-84.
Leite, et al., "IgG1 Antibodies to Acetylcholine Receptors in 'Seronegative' Myasthenia Gravis." Brain. May 31, 2008.
Liguori, et al., "Morvan's Syndrome: Peripheral and Central Nervous System and Cardiac Involvement with Antibodies to Voltage-Gated Potassium Channels." Brain. Dec. 2001; 124(Pt 12): 2417-26.
Nagado, et al., "Potassium Current Suppression in Patients with Peripheral Nerve Hyperexcitability." Brain. Nov. 1999; 122(Pt 1):2057-66.
Pavlou, et al., "Analysis of Interactions of the Adhesion Molecule TAG-1 and its Domains with Other Immunoglobulin Superfamily Members." Mol Cell Neurosci. Jul. 2002; 20(3):367-81.
Poliak, et al., "Caspr2 New Member of the Neurexin Superfamily, is Localized at the Juxtaparanodes of Myelinated Axons and Associates with K+ Channels," Neuron. Dec. 1999; 24(4):1037-47.
Poliak, et al., "Juxtaparanodal Clustering of Shaker-Like K+ Channels in Myelinated Axons Depends on Caspr2 and TAG-1." The Journal of Cell Biology. Sep. 15, 2003;162(6):1149-60.
Schott, et al., "Amnesia, Cerebral Atrophy, and Autoimmunity." Lancet. Apr. 12, 2003;361(9365):1266.
Schulte, et al., "The Epilepsy-Linked Lgi1 Protein Assembles into Presynaptic Kv1 Channels and Inhibits Inactivation by Kvbeta1." Neuron. Mar. 2, 2006; 49(5):697-706.
Scott, et al., "Antibodies Specific for Distinct Kv Subunits Unveil a Heterooligomeric Basis for Subtypes of Alpha-Dendrotoxin-Sensitive K_Channels in Bovine Brain." Biochemistry. Feb. 22, 1994;33(7):1617-23.

(Continued)

*Primary Examiner* — Kimberly A. Ballard
(74) *Attorney, Agent, or Firm* — Zhi-Xiang (Alex) Oh; Stoel Rives, LLP

(57) ABSTRACT

The invention relates to a method of diagnosing an autoimmune neurological disorder in a mammal comprising the step of detecting, in a bodily fluid sample from the mammal, autoantibodies to an epitope of at least one Kv1-complex protein; and related methods, assay kits, isolated or purified autoantibody or antibody fragments, or uses thereof.

20 Claims, 14 Drawing Sheets

(56) References Cited

OTHER PUBLICATIONS

Figure 1:
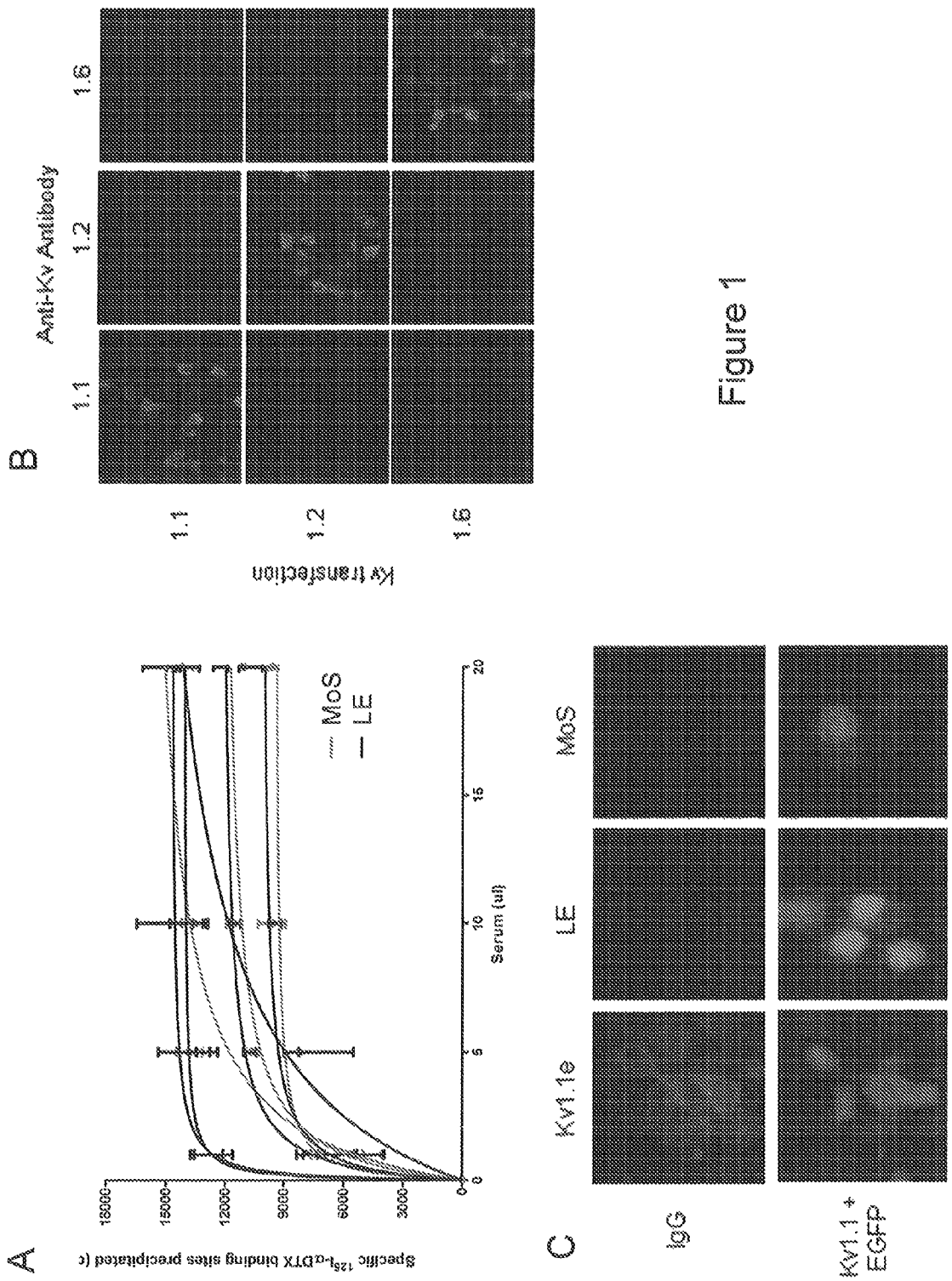

Shamotienko, et al., "Subunit Combinations Defined for K+ Channel Kv1 Subtypes in Synaptic Membranes from Bovine Brain." Biochemistry. Jul. 8, 1997;36(27):8195-201.

Shillito, et al., "Acquired Neuromyotonia: Evidence for Autoantibodies Directed Against K+ Channels of Peripheral Nerves," Annals of Neurology. Nov. 1995; 38(5):714-22.

Sinha, et al., "Autoimmune Aetiology for Acquired Neuromyotonia (Isaacs' Syndrome)," Lancet. Jul. 13, 1991;338(8759):75-7.

Sirerol-Piquer, et al., "The Epilepsy Gene LGI1 Encodes a Secreted Glycoprotein that Binds to the Cell Surface." Hum Mol Genet. Dec. 1, 2006;15(23):3436-45. Epub Oct. 26, 2006.

Smart, et al., "Deletion of the K(V)1.1 Potassium Channel Causes Epilepsy in Mice." Neuron. Apr. 1998; 20(4):809-19.

Strauss, et al., "Recessive Symptomatic Focal Epilepsy and Mytatnt Contactin-Associated Protein-Like 2." The New England Journal of Medicine. Mar. 30, 2006;354(13):1370-7.

Tomimitsu, et al., "Mechanism of Action of Voltage-Gated K+ Channel Antibodies in Acquired Neuromyotonia." Annals of Neurology. Sep. 2004; 56(3):440-4.

Traka, et al., "Association of TAG-1 with Caspr2 is Essential for the Molecular Organization of Juxtaparanodal Regions of Myelinated Fibers." J Cell Biol. Sep. 15, 2003;162(6):1161-72.

Vincent, et al., "Autoimmune Channelopathies and Related Neurological Disorders." Neuron. Oct. 5, 2006; 52(2):123-38.

Vincent, et al., "Potassium Channel Antibody-Associated Encephalopathy: A Potentially Immunotherapy-Responsive Form of Limbic Encephalitis." Brain. Mar. 2004; 137(pt 3):701-12.

Waters, et al., "Aquaporin-4 Antibodies in Neuromyelitis Optica and Longitudinally Extensive Transverse Myelitis." Archives of Neurology. Jul. 2008;65(7):913-9.

Zuberi, et al., "A Novel Mutation in the Human Voltage-Gated Potassium Channel Gene (Kv1.1) Associates with Episodic Ataxia Type 1 and Sometimes with Partial Epilepsy." Brain. May 1999; 122(Pt 5):817-25.

International Search Report issued Mar. 3, 2010 in International Application No. PCT/GB2009/051441.

International Preliminary Report on Patentability and Written Opinion issued Apr. 26, 2011 in International Application No. PCT/GB2009/051441.

* cited by examiner

Figure 7
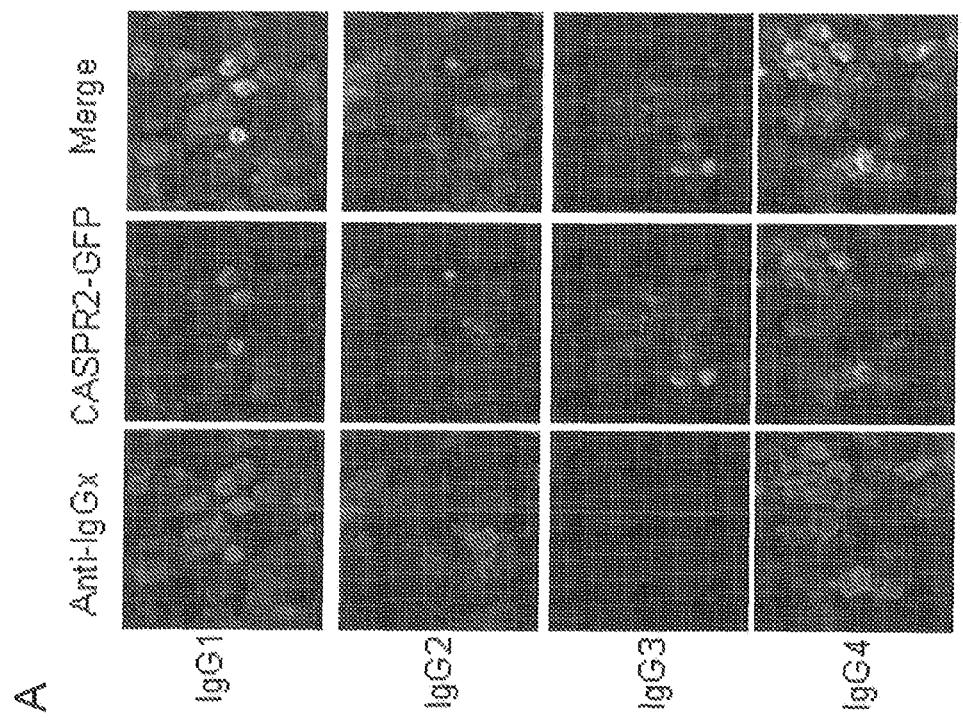
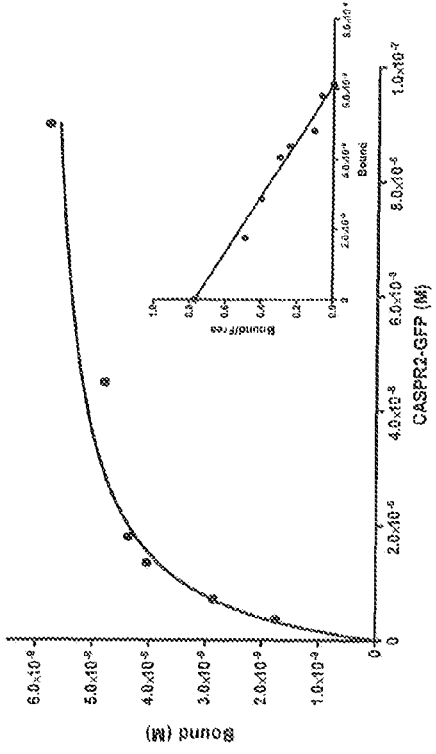
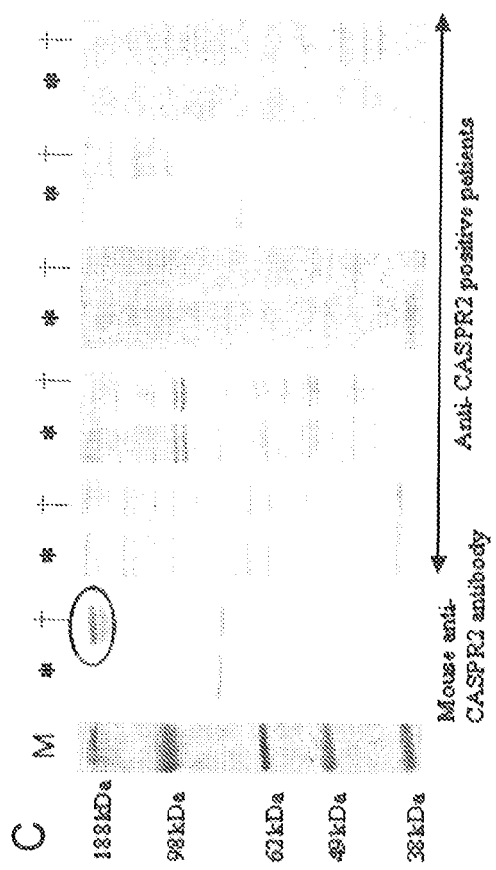

Figure 10
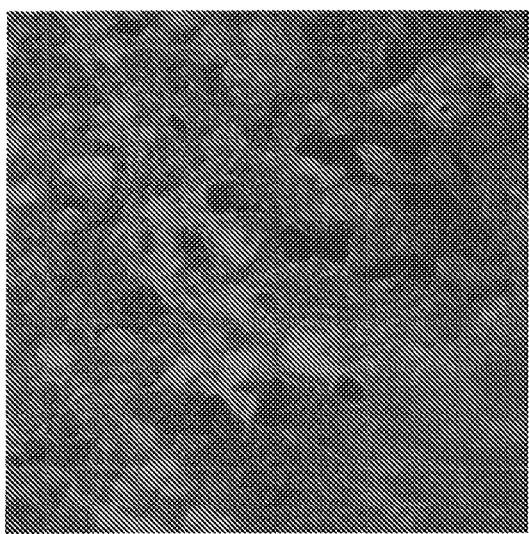
A
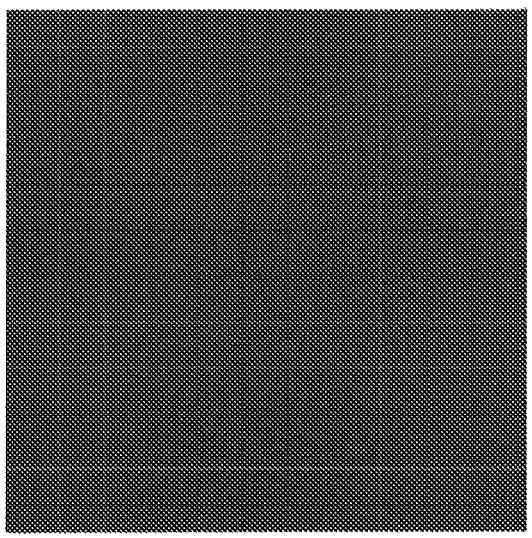
B

Figure 13

|  | Males | Females | Total | VGKC Ab neg |
|---|---|---|---|---|
| Total numbers | 78 | 30 | 108 | 8 |
| Median age, range | 54, 19-78 | 60, 17-83 | 60, 17 - 83 | |
| Non thymic tumours* | 5 | 2 | 7 | 0 |
| Thymomas** | 8 | 3 | 11 | 0 |
| Limbic encephalitis or epilepsy | 49 | 16 | 65 | 0 |
| Morvan's syndrome | 11 | 1 | 12 | 0 |
| Neuromyotonia | 15 | 10 | 25 | 8 |
| Epilepsy or others | 3 | 3 | 6 | 0 |

Figure 14

| All patients | Lgi1 | CASPR2 | TAG-1 | Accessory protein not yet identified |
|---|---|---|---|---|
| Total number | 39 | 27 | 4 | 38 |
| Thymic malignancies | 0 | 10 | 0 | 1 |
| Limbic encephalitis or epilepsy | 36 | 7 | 1 | 21 |
| Morvan's syndrome | 2 | 10 | 0 | 0 |
| Neuromyotonia | 0 | 8 | 3 | 14 |
| Other syndrome | 1 | 2 | 0 | 3 |
| VGKC-Ab negative | 0 | 0 | 1 | 7 |

*The majority were not currently-active

SEQUENCE LISTING

```
<160> NUMBER OF SEQ ID NOS: 2

<210> SEQ ID NO 1
<211> LENGTH: 39
<212> TYPE: DNA
<213> ORGANISM: Artificial Sequence
<220> FEATURE:
<223> OTHER INFORMATION: PCR primer

<400> SEQUENCE: 1
gatcgctagc ccaccatgga atcagaaaga agcaaaagg                    39

<210> SEQ ID NO 2
<211> LENGTH: 37
<212> TYPE: DNA
<213> ORGANISM: Artificial sequence
<220> FEATURE:
<223> OTHER INFORMATION: PCR primer

<400> SEQUENCE: 2
gatcctcgag tcatgcgctt aagtcaacta tgacatg                      37
```

NEUROLOGICAL AUTOIMMUNE DISORDERS

The present invention relates to autoimmune disorders, and in particular to methods of diagnosing such disorders in mammals. Also provided by the present invention are kits for use in said diagnosis, and methods and compositions for detecting autoantibodies.

Voltage-gated potassium channel (VGKC) antibodies are associated with three main clinical syndromes: neuromyotonia (NMT), Morvan's syndrome (MoS) and limbic encephalitis (LE). NMT describes peripheral nerve hyperexcitability syndromes causing muscle cramps and stiffness, and sometimes pain. MoS describes NMT plus autonomic features, for instance excessive sweating, constipation, cardiac irregularities, and central nervous system features, particularly confusion, hallucinations and insomnia. LE associated with anti-VGKC antibodies includes the central nervous system (CNS)-restricted features of amnesia, personality or psychiatric disorders, and seizures (epilepsy). These conditions (particularly MoS) can be associated with thymic or other tumours (lung carcinoma, lymphoma, gynaecological malignancies) but anti-VGKC antibody associated LE is mainly non-paraneoplastic. All three syndromes have a subacute onset and may be immunotherapy-responsive. In addition, there is recognition of these antibodies in some patients presenting with other clinical syndromes such as idiopathic epilepsy. Most patients so far are adults, but some children with these antibodies and LE or epilepsy have been identified. As already demonstrated in vivo with NMT [1], much evidence supports a pathogenic role of LE and MoS immunoglobulin G (IgG). Firstly, patients often experience a prompt clinical recovery following plasma exchange [2, 3]. Secondly, the antibody titres in an individual patient correlate well with alterations in clinical state [2, 3]. Thirdly, the patient IgG binds the hippocampus, the anatomical region to which almost all CNS clinical features can be localised [2-4]. Around 500 patients with anti-VGKC antibodies and CNS features have been diagnosed in the last 5 years in the UK (A Vincent, unpublished observations).

Patient sera which immunoprecipitate iodinated alpha-dendrotoxin ($I^{125}$-αDTX)-labelled digitonin-solubilised mammalian brain homogenate are designated as containing anti-VGKC antibodies [5, 6]. Voltage-gated potassium channels consist of a number of structurally different families of channels including the Kv1 (Shaker) subtype. Kv1 alpha subunits may homo- or heterotetramerise exclusively with other Kv1 subunits to form active channels. αDTX binds Kv1.1, 1.2 and 1.6 channels which are all present in brain tissue and Kv1.1 and 1.2 are found in peripheral nerves. These 3 subunits may have their function and surface expression modulated by Kv1.4 and by Kvβ1, 2 and 3, where Kvβ2 is the most abundant Kvβ member in brain tissue.

Patients with LE and MoS generally have higher anti-VGKC antibody titres than NMT patients. The antigenic targets and functional effects of NMT anti-VGKC antibodies have previously been studied in detail and NMT IgG has been shown to bind expressed Kv1s and downregulate Kv1 currents [5-7] but only one study has examined LE or MoS anti-VGKC antibodies [8].

Recently, a number of novel Kv1-interacting proteins have been described [9, 10]. The present invention shows that Kv1-complex proteins, for example the three Kv1-complex proteins CASPR2 (contactin associated protein 2), Lgi1 (leucine-rich glioma inactivated gene 1), TAG1 (transient axonal glycoprotein-1, also known as contactin 2), and not necessarily the Kv1 proteins themselves, are the targets for autoantibodies from some patients with LE and MoS.

According to a first aspect, the present invention provides a method of diagnosing an autoimmune neurological disorder in a mammal comprising the step of detecting, in a bodily fluid sample from the mammal, autoantibodies to an epitope of at least one Kv1-complex protein.

The at least one Kv1-complex protein may be complexed/bound with other proteins of the Kv1-complex, or the at least one Kv1-protein may be separate of the Kv1-complex, for example not co-localised, or not physically bound to the complex. The autoantibodies may bind to the normally complexed/bound proteins even when they are not in a complexed/bound state.

The Kv1-complex protein may be an essential or non-essential accessory protein to Kv1. The Kv1-complex protein may comprise at least one of Kv1, CASPR2, Lgi1 and TAG1. The Kv1-complex protein may comprise at least one of CASPR2, Lgi1 and TAG1. In one embodiment, the Kv1-complex proteins may not comprise Kv1.

CASPR2, Lgi1 and TAM are proteins that have been shown to interact or be physically linked with Kv1. For example, CASPR2 and Tag1 are necessary for the localisation of Kv1 proteins at the nodes of Ranvier.

The Kv1-complex protein may comprise, or consist essentially of, CASPR2. The Kv1-complex protein may comprise, or consist essentially of, Lgi1. The Kv1-complex protein may comprise, or consist essentially of, TAG1. The Kv1-complex protein may comprise, or consist essentially of, a protein of the Kv1-complex other than CASPR2, Tag1, Lgi1, and Kv1.

Preferably the autoimmune neurological disorder is limbic encephalitis, Morvan's syndrome, neuromyotonia or a related condition. Preferably the neurological disorder is limbic encephalitis or Morvan's syndrome, or neuromyotonia. Where the neurological disorder is limbic encephalitis, the dominant feature of the neurological disorder may comprise seizures, for example epilepsy, or amnesia or psychiatric disorder alone.

Where the autoimmune neurological disorder is Morvan's syndrome and/or neuromyotonia, the Kv1-complex protein may comprise CASPR2. Autoantibodies directed to CASPR2 may be indicative of, or associated with, an increased risk of thymic malignancies, and/or other malignancies.

Where the autoimmune neurological disorder is limbic encephalitis or predominantly epilepsy, the Kv1-complex protein may comprise Lgi1.

Where the autoimmune neurological disorder is neuromyotonia and/or limbic encephalitis and/or epilepsy, the Kv1-complex protein may comprise TAG1.

Where the autoimmune neurological disorder is the Kv1-complex protein may comprise CASPR2 and TAG1.

Preferably, the method of the invention further comprises the steps of a) contacting the bodily fluid with the Kv1-complex protein or an antigenic determinant thereof; and b) detecting any antibody-antigen complexes formed between Kv1-complex protein or an antigenic determinant thereof and antibodies present in the bodily fluid, wherein presence of said complex is indicative of an autoimmune neurological disorder, preferably of limbic encephalitis, Morvan's syndrome, neuromyotonia or a related condition.

Preferably the method of the invention is performed in combination with an assessment of clinical symptoms. The combination of the method of the invention and an analysis of clinical symptoms may be used to determine the specific neurological disorder an individual has.

The autoantibody may be detected by any immunological assay technique, of which many are well know in the art.

Examples of suitable techniques include ELISA, radioimmunoassay, a competition assay, an inhibition assay, a sandwich assay and the like. In general terms, such assays use an antigen, which may be immobilised on a solid support. A sample to be tested is brought into contact with the antigen and if autoantibodies specific to the antigen are present in a sample they will immunologically react with the antigen to form autoantibody-antigen complexes, which may then be detected or quantitatively measured. Alternatively, the antigen can be expressed on the surface or within a cell which is permeabilised [16]. Detection of autoantibody-antigen complexes may be carried out using a secondary anti-human immunoglobulin antibody, typically anti-IgG or anti-human IgM, which recognises general features common to all human IgGs or IgMs respectively. The secondary antibody is usually conjugated to an enzyme such as, for example, horseradish peroxidise (HRP), so that detection of an autoantibody/antigen/secondary antibody complex is achieved by addition of an enzyme substrate and subsequent colourmetric, chemiluminescent or fluorescent detection of the enzymatic reaction products, or it may be conjugated to a fluorescent signal [16]. Preferably the method uses a secondary antibody which is tagged or labelled anti-IgG antibody. Preferably the anti-IgG antibody is labelled with a reporter molecule. The reporter molecule may by a heavy metal, a fluorescent or luminescent molecule, a radioactive tag or an enzymatic tag. An enzymatic tag may be HRP.

Preferably the intensity of the signal from the anti-IgG antibody is indicative of the relative amount of the Kv1-complex protein autoantibody in the bodily fluid when compared to a positive or negative control.

According to a further aspect, the invention provides an assay kit for diagnosing an autoimmune neurological disorder in a mammal comprising at least one epitope of at least one Kv1-complex protein.

According to a further aspect, the invention provides an assay kit for detecting an increased risk for an autoimmune neurological disorder in a mammal comprising at least one epitope of at least one Kv1-complex protein.

Preferably the kit comprises instruction to use the kit. Preferably, the kit also comprises means for contacting the at least one epitope of at least one Kv1-complex protein with a bodily fluid sample from a mammal. Preferably the neurological disorder is limbic encephalitis, Morvan's syndrome, neuromyotonia or a related condition.

A related condition may comprise amnesia without major seizures, epilepsy without major amnesia and/or personality/psychiatric disorder without major amnesia and/or thymic malignancies.

A kit according to the invention may further comprise a standard solution for preparing a calibration curve.

According to another aspect, the invention provides an isolated or purified autoantibody specific for an epitope of at least one Kv1-complex protein. Such an antibody may be isolated from a bodily fluid sample.

According to yet another aspect, the invention provides an isolated or purified antibody or antibody fragment specific for at least one Kv1-complex protein autoantibody. Such an antibody may be used as a medicament, or in the preparation of a medicament for the treatment of a neurological disorder and/or a related condition. Preferably the neurological disorder is limbic encephalitis, Morvan's syndrome, or neuromyotonia. Such an antibody may be included in a pharmaceutical composition together with a pharmaceutically acceptable carrier, excipient or diluent. A related condition may comprise amnesia without major seizures, epilepsy without major amnesia and/or personality/psychiatric disorder without major amnesia and/or thymic malignancies.

Monoclonal or polyclonal antibodies or antibody fragments may be prepared using techniques well known to the man skilled in the art.

An antibody specific for the Kv1-complex protein autoantibodies may also be used in a diagnostic kit to detect neurological disorders such as limbic encephalitis, Morvan's syndrome, neuromyotonia, or a related condition, or to determine an increased risk of such conditions, or of thymic malignancy.

A bodily fluid for use in any aspect of the invention may comprise plasma, serum, whole blood, urine, sweat, lymph, faeces, cerebrospinal fluid, or nipple aspirate. Preferably the bodily fluid is serum or plasma.

According to a further aspect, the invention provides a method of treating a patient suffering from a neurological disorder, such as limbic encephalitis, Morvan's syndrome, or a related condition, comprising administering to said patient an effective amount of an antibody according to the invention or at least one Kv1-complex protein or epitope thereof.

According to a yet further aspect, the invention provides a method of identifying compounds capable of alleviating or treating a neurological disorder, such as limbic encephalitis, Morvan's syndrome, or a related condition, comprising the steps of contacting a candidate compound in the presence of at least one Kv1-complex protein or an epitope thereof and an antibody capable of binding at least one Kv1-complex protein, wherein a compound that prevents binding of said antibody to at least one Kv1-complex protein or an epitope thereof is a candidate for treating neurological disorders.

The skilled man will appreciate that any of the preferable features discussed above can be applied to any of the aspects of the invention.

Preferred embodiments of the present invention will now be described, merely by way of example, with reference to the following figures and examples.

FIG. 1—LE or MoS sera precipitate Kv1s from rabbit cortex extract but do not bind directly to Kv1s.

A. LE and MoS sera titrations precipitate high levels of $I^{125}$-αDTX-labelled Kv1s in solubilised rabbit cortex homogenate.

B. Anti-Kv1.1, 1.2 and 1.6 antibodies (1:500), that bind to intracellular epitopes, binding to permeabilised Kv1.1, 1.2 or 1.6 transfected cells. Visualised with anti-rabbit IgG (1:750; 568 nm). Good specificity of anti-Kv1 antibodies is observed.

C. HEK cells cotransfected with Kv1.s and enhanced green fluorescence protein (EGFP) (488 nm). LE (n=15) and MoS (n=6) sera (1:20) applied to Kv1.1-EGFP co-expressing HEK cells were not detected bound to the surface using anti-human IgG Alexa Fluor (568 nm). No binding was seen after cotransfection of Kv1 subunit combinations, including 1.1, 1.2, 1.4, 1.6 and β2. However, an antibody directed against an extracellular epitope of Kv1.1 (1:100) did bind to Kv1.1 transfected cells.

Figure 2:
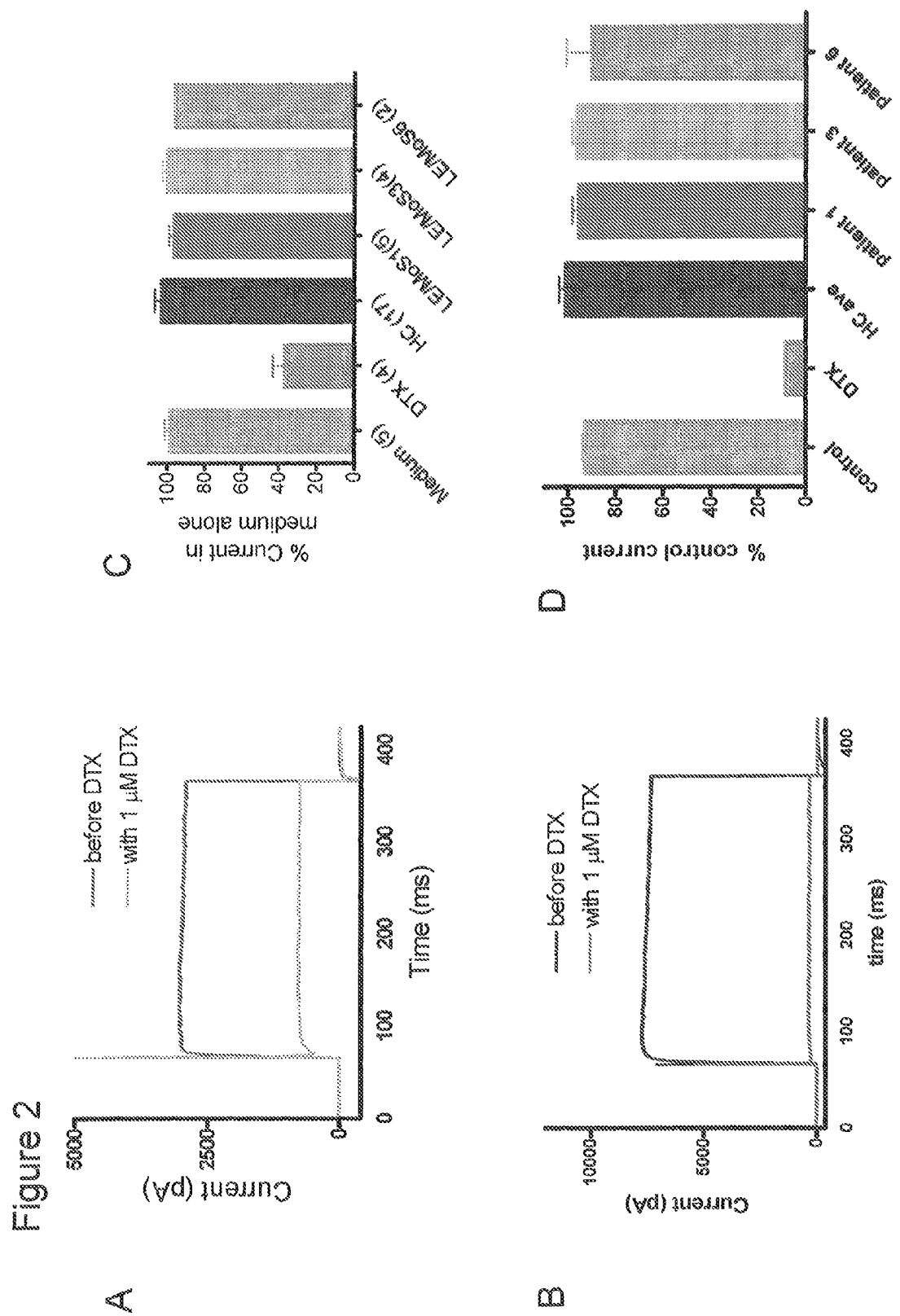

FIG. 2—Functional, αDTX-sensitive Kv1 currents are not affected by acute application of LE and MoS IgG.

A. HEK-293 cells transfected with Kv1.1 express αDTX-sensitive currents.

B. Similarly, HEK-293 cells transfected with Kv1.6 express large amplitude αDTX-sensitive currents; these currents were of significantly larger amplitude than Kv1.1-mediated currents.

C and D. Kv1.1 (C) and Kv1.6 (D) currents are not affected by acute application of control or patient sera.

Figure 3:
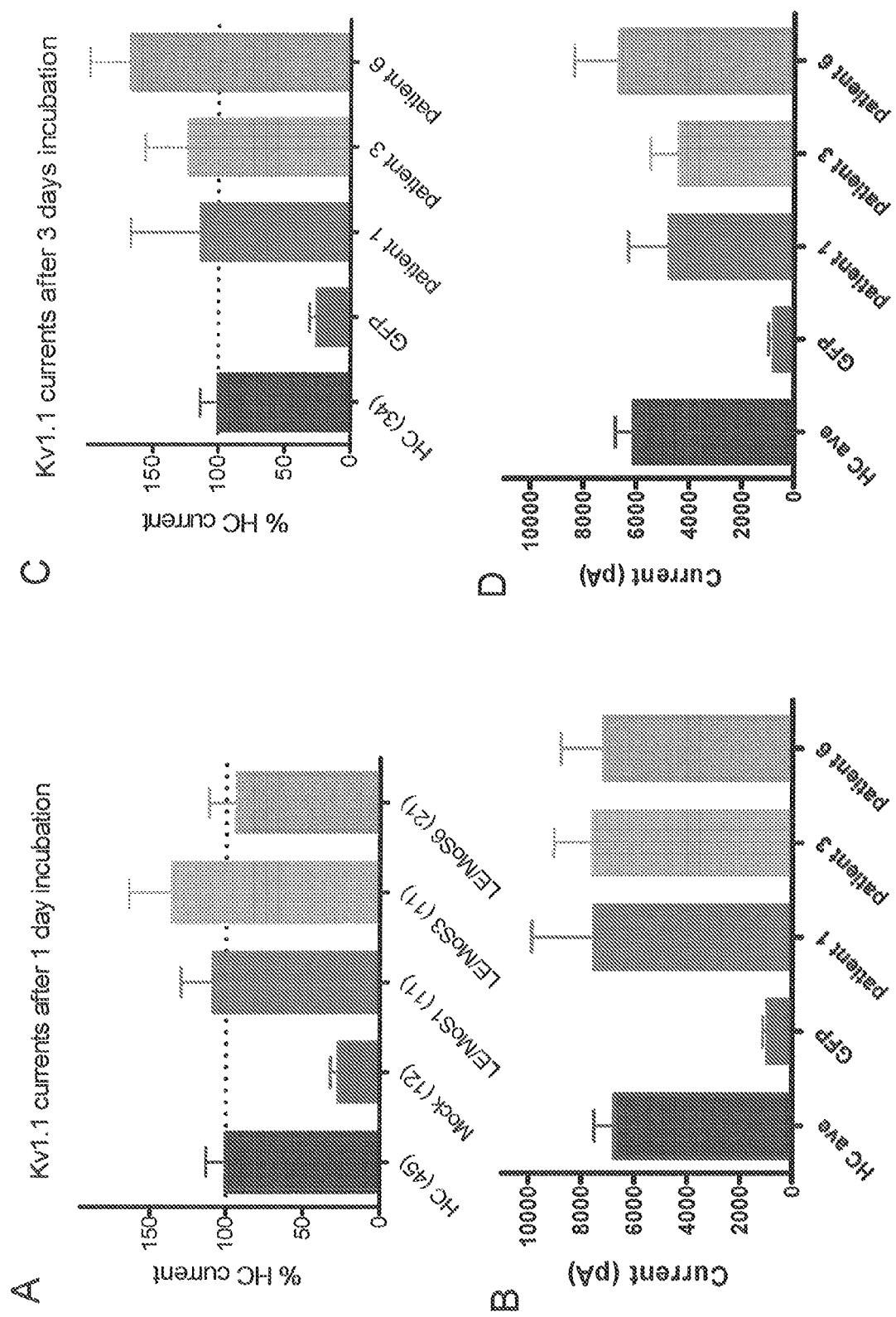

FIG. 3—αDTX-sensitive Kv1 currents are not affected by chronic application of Le and MoS IgG A and B: αDTX-sensitive Kv1.1 (A) and Kv1.6 (B) mediated currents were not significantly reduced following incubation with patient sera at 1 day (p>0.05, one-way ANOVA).

C and D: Likewise, no significant reduction in Kv1.1 (C) or Kv1.6 (D) mediated currents was observed after 3-day incubation with patient sera (p>0.05, one-way ANOVA).

Figure 4:
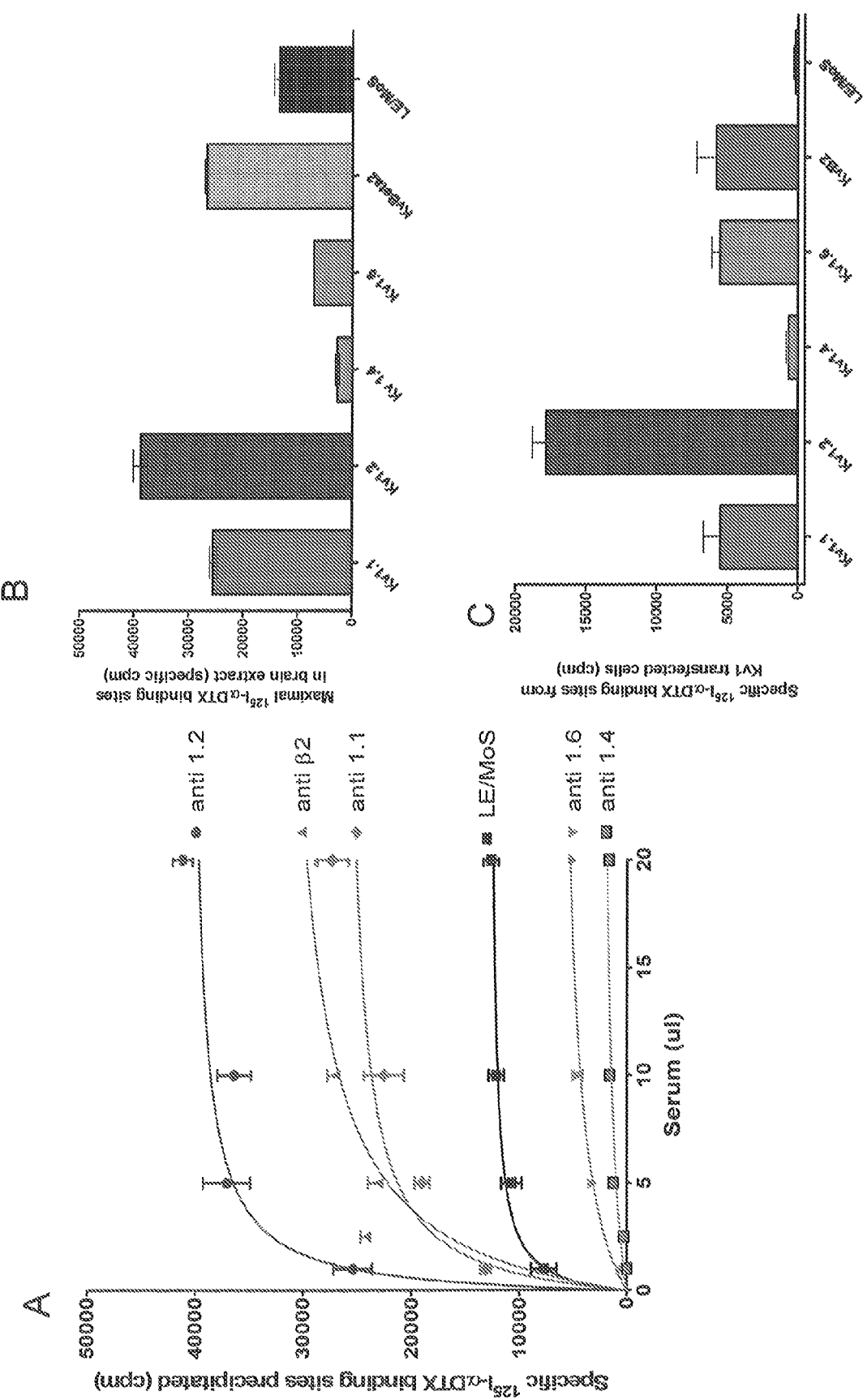

FIG. 4—Patient sera and anti-Kv1s precipitate different amounts of $I^{125}$-αDTX-labelled Kv1s from rabbit cortex extracts and patient sera do not precipitate $I^{125}$-αDTX-labelled Kv1s from transfected cell extracts.

A. Multiple anti-Kv1 commercial antibodies, LE (n=5) and MoS (n=3) sera titrations with 50,000 cpm of $I^{125}$-αDTX-labelled Kv1s from rabbit cortex extract in each assay (n=3 experiments). Healthy control values have been subtracted to generate specific data.

B. Maximum number of $I^{125}$-αDTX binding sites precipitated by each anti-sera from FIG. 4A, predicted with a one site binding hyperbola (GraphPad Prism V5).

C. $I^{125}$-αDTX-labelled Kv1.1/1.2/1.4/1.6/β2 extracted from transfected cells are not precipitated by LE or MoS sera (5 ul) but are precipitated by anti-Kv1 antibodies (5 ul; n=5 experiments). Non-specific binding, using healthy control serum or an irrelevant anti-rabbit antibody, has been subtracted.

Figure 5:
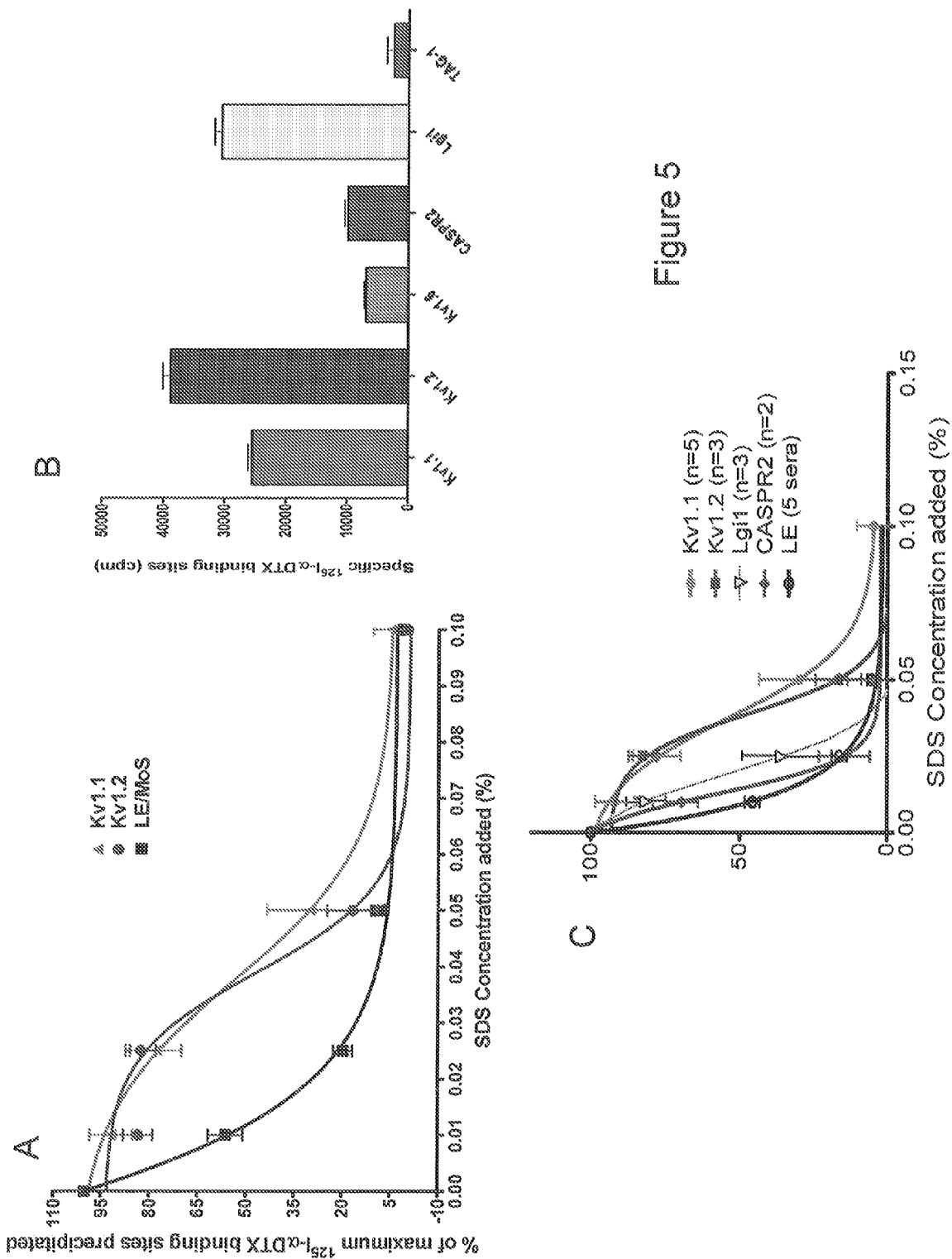

FIG. 5—LE and MoS serum binding site dissociates from $^{125}$I-αDTX-complexes. CASPR2 antibodies coimmunoprecipitate $^{125}$I-αDTX from brain extract and dissociate similarly to LE/MoS sera.

A. LE (n=5) and MoS (n=3) IgG binding to $I^{125}$-αDTX-labelled, digitonin-solubilised rabbit cortex complexes shows greater sensitivity to sodium dodecyl sulphate (SDS) than anti-Kv1.1/1.2 IgG binding (results of all 8 sera combined).

B. An anti-CASPR2 antibody precipitates 20% of the total $I^{125}$-αDTX binding sites from labelled brain homogenate, similar to that found with LE and MoS sera (FIG. 4a). In addition, anti-LgI1 antibody precipitates >60% of the total $I^{125}$-αDTX binding sites, and anti-TAG1 antibody precipitates <10% total $I^{125}$-αDTX binding sites. Thus a high proportion of the total $I^{125}$-αDTX binding sites are complexed with Lgi1, and a small proportion with TAG1.

C. In a similar experiment to that shown in A, the dissociation pattern of CASPR2 antibodies (mean of 2 experiments) and of Lgi1 antibodies (mean of 3 experiments) are similar to that of the LE patients' IgG (n=5) as compared with the anti-Kv1.1/1.2 IgG binding.

Figure 6:
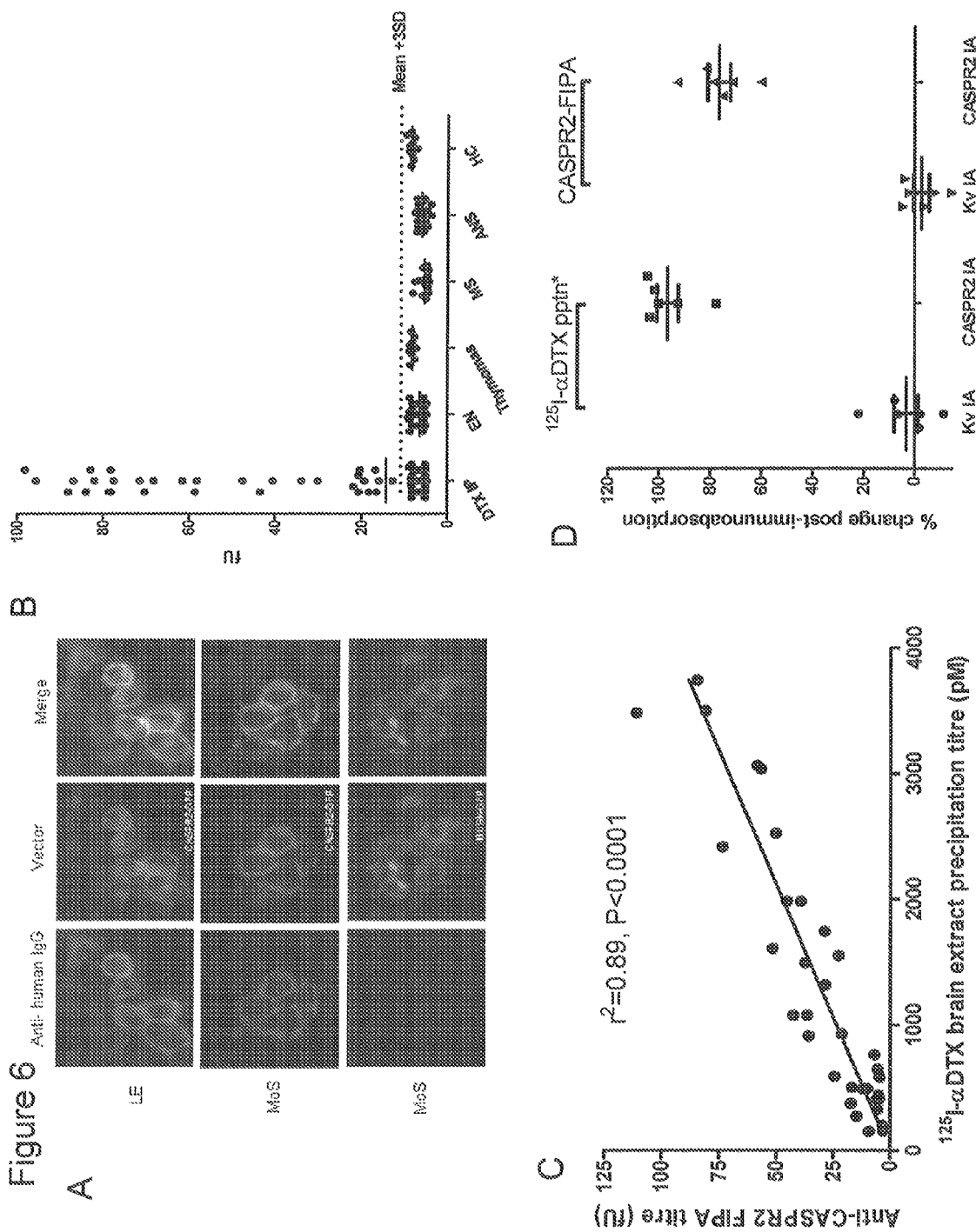

FIG. 6—Some LE/MoS sera bind directly to the extracellular domain of CASPR2. Binding in solution is highly specific and these titres correlate with $^{125}$I-αDTX immunoprecipitation titres.

A. LE and MoS sera (1:100) bind the extracellular domain of expressed CASPR2 (×1000 magnification).

B. 100 fU (fluorescent units) of CASPR2-EGFP extract were incubated with 5 ul patient sera and immunoprecipitated. Of 188 sera known to immunoprecipitate $I^{125}$-αDTX-labelled brain homogenate, 32 (18%) also precipitated CASPR2-EGFP. Sera from patients with other neurological diseases that did not precipitate $I^{125}$-αDTX-binding sites were not positive using the CASPR2-GFP fluorescent immunoprecipitation assay (FIPA). These included encephalopathies (EN), thymomas, multiple sclerosis (MS), autonomic disease (ANS) and healthy controls (HC). These sera do not precipitate or bind the extracellular domain of MuSK-EGFP (FIG. 6a, lower panel).

C. Anti-CASPR2 FIPA titres linearly correlate with $I^{125}$-αDTX brain homogenate immunoprecipitation titres (Spearman correlation $r^2$=0.89, P<0.0001).

D. Immunoadsorption of anti-CASPR2 positive sera against the extracellular domain of CASPR2 obviates precipitation from $I^{125}$-αDTX-brain extract*. However, absorption against the extracellular domains of Kv1.1-1.2-1.6 expressing HEK cells does not remove $I^{125}$-αDTX-brain extract precipitation.

FIG. 7—CASPR2 antibodies are of IgG1 and IgG4 subclasses and of high affinity. They do not bind to linearised CASPR2 on western blots.

A. Subclass-specific secondary anti-IgGs binding to anti-CASPR2 antibodies already bound to CASPR2-GFP expressing HEK cells allow quantification of relative quantities of anti-CASPR2 antibody subclasses.

B. Scatchard analyses of antibody affinities were calculated by titrating CASPR2-GFP extract against a non-saturating volume of patient serum (n=5). Kd values of $1.2 \times 10^{-8}$M (±standard deviation $0.54 \times 10^{-8}$M) were obtained.

C. CASPR2 has a molecular weight of 180 KDa. Mouse anti-CASPR2 antibody detects a 180 kDa band in CASPR2 extract (†, circled), not in Kv1.1/1.2/1.6 extract (*). Proven anti-CASPR2 positive sera do not bind a consistent band in CASPR2 extract (†) in western blots.

Figure 8:
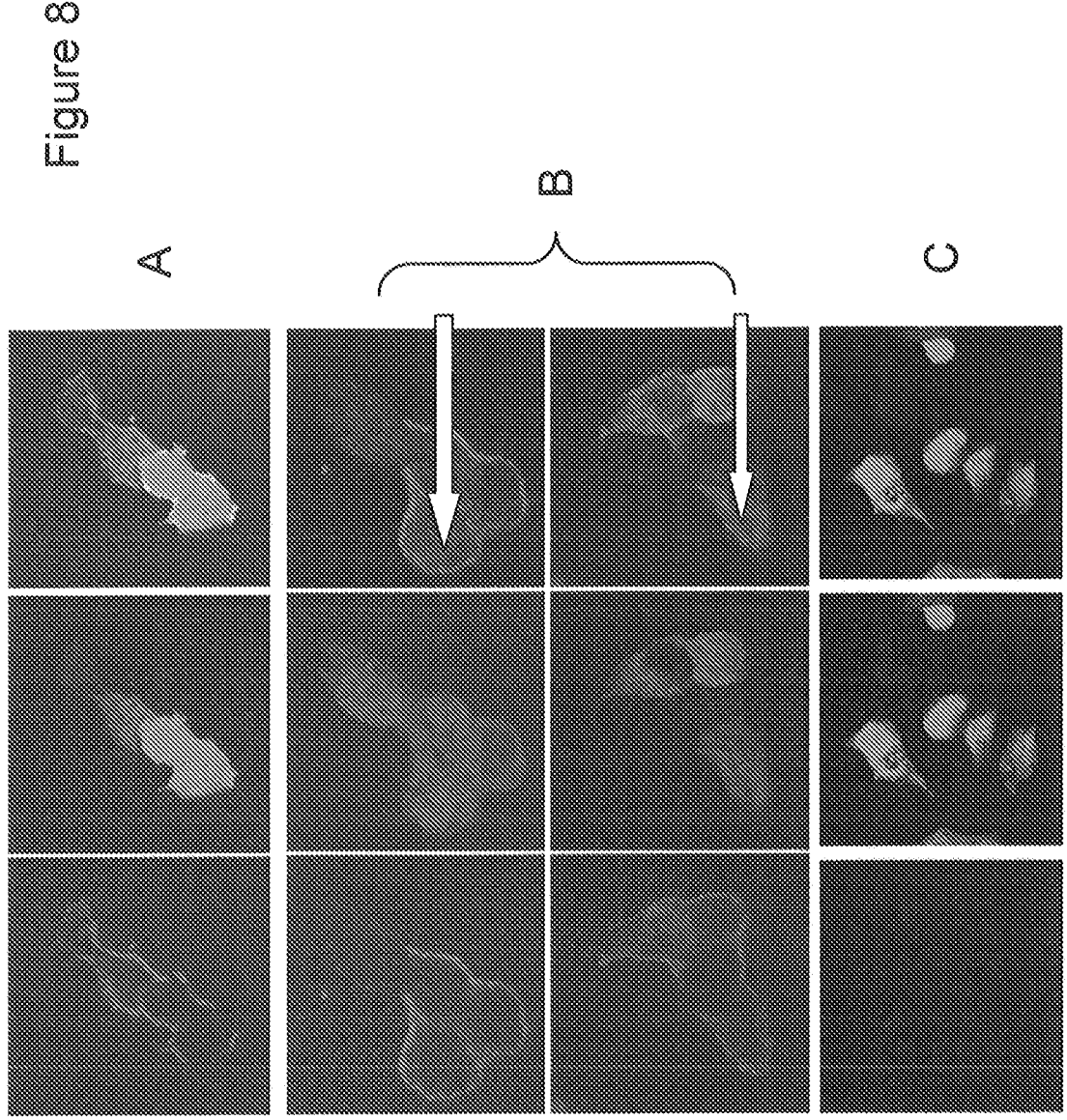

FIG. 8—Binding of serum IgG to TAG1 transfected HEK cells.

A. Commercial antibody binding to TAG1 transfected cells demonstrated that it was expressed at the cell surface.

B. Example of NMT patient serum IgG binding to the surface of TAG1-HEK (EGFP positive) cells. Of the 108 sera tested from patients with confirmed clinical diagnosis only 4 bound clearly to TAG1. Three of these were from patients with neuromyotonia.

C. Control sera (n=40) did not bind.

Figure 9:
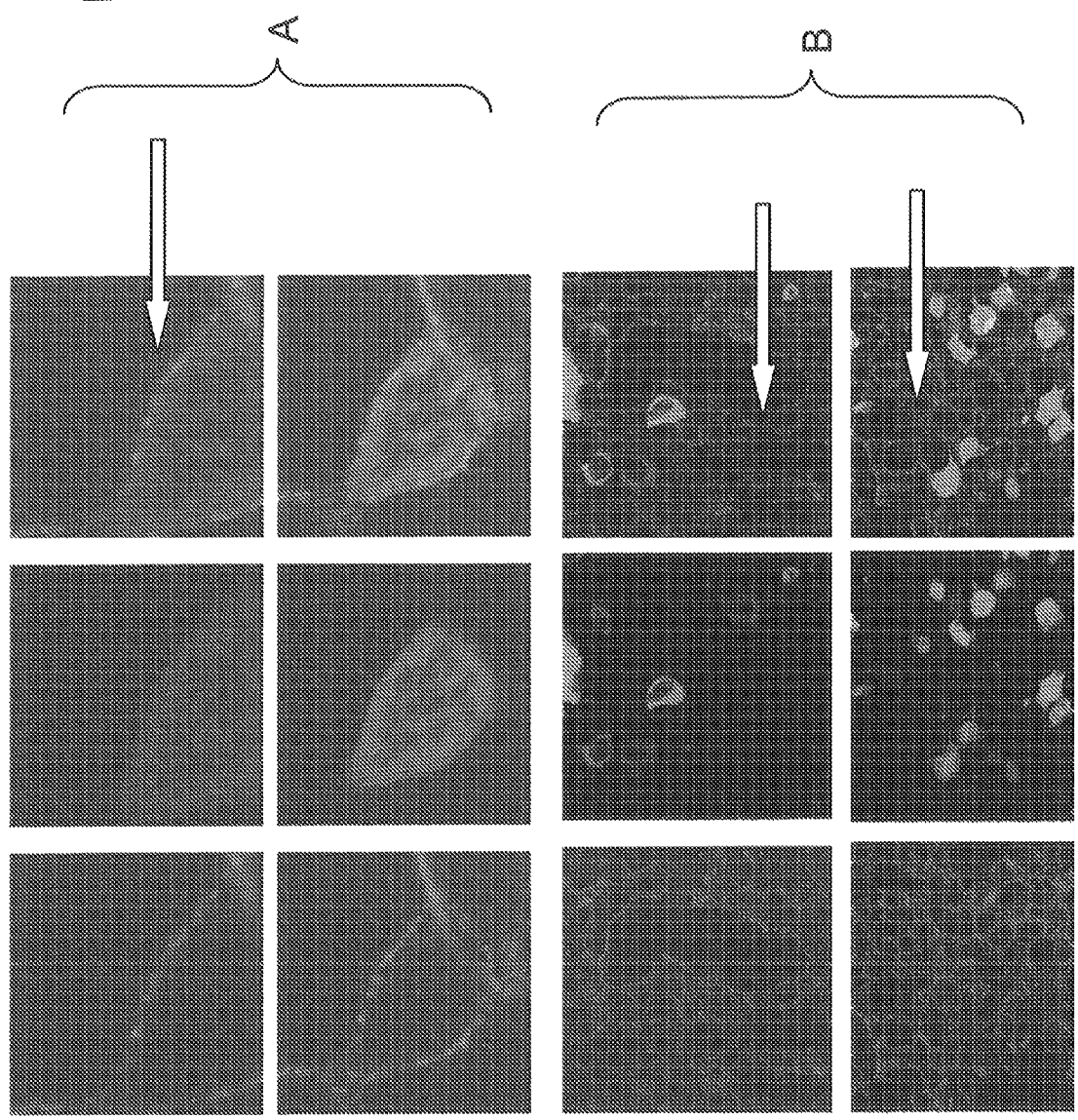

FIG. 9—Binding of serum IgG to Lgi1 transfected HEK cells.

A. Two examples of serum IgG binding to Lgi1-HEK cells. Of the 108 sera tested, 39 bound to Lgi1-transfected cells. Control sera (other diseases, healthy individuals) did not bind (n=70).

B. However, the binding was not exclusively to the EGFP co-transfected HEK cells which suggests that (as previously reported [24, 25]), the Lgi1 is secreted into the medium and some of it binds to the surface of both the transfected (EGFP positive, green) and untransfected (EGFP negative, not green) HEK cells.

FIG. 10—Binding of serum IgG with Lgi1 reactivity to untransfected HEK cells.

A—Lgi1 media, untransfected HEK cells incubated for 1 hour with supernatant from Lgi1-transfected HEK cells were bound by patient serum IgG previously identified as binding to Lgi1 (FIG. 9).

B—MUSK media, untransfecteed HEK cells incubated for 1 hour with supernatant from MuSK-transfected HEK cell supernatants were not bound by these patients' IgG.

Figure 11:
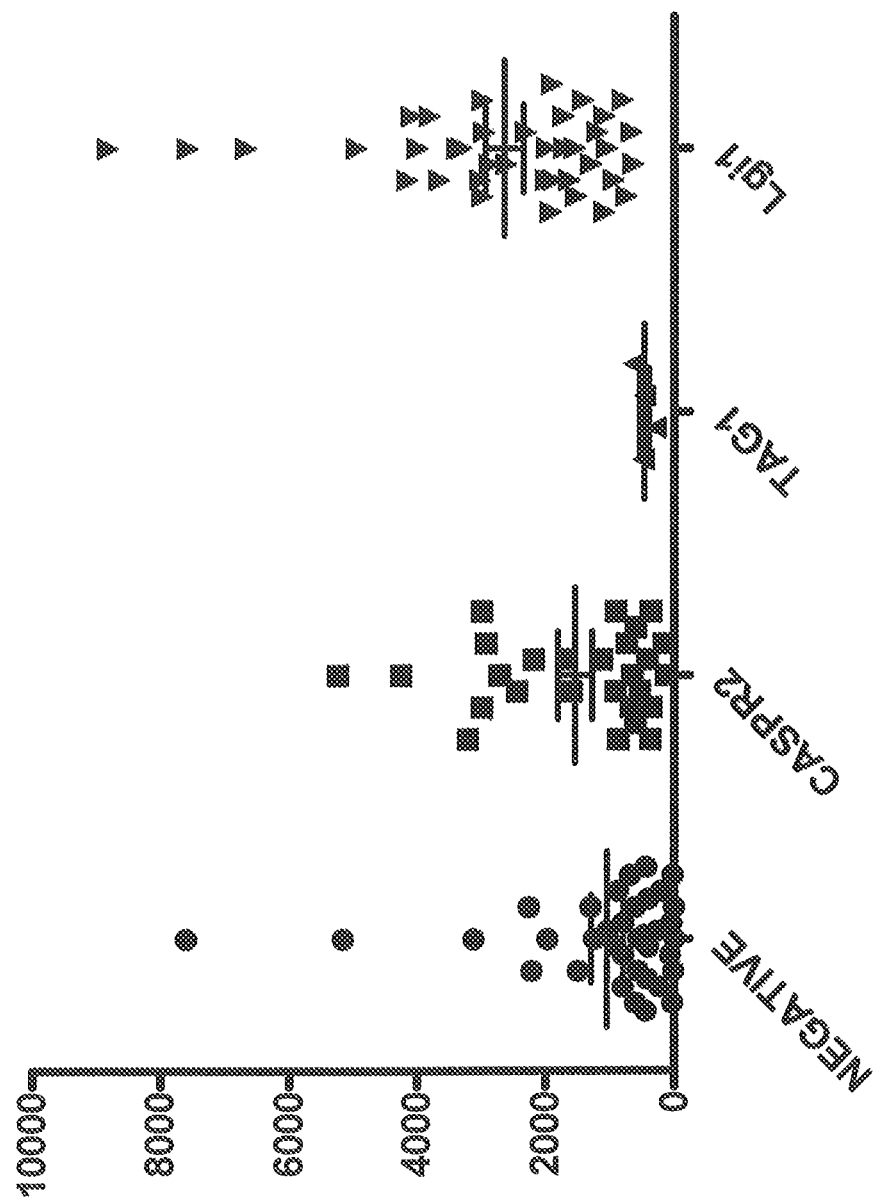

FIG. 11—VGKC antibody titres from routine clinical testing are shown in the patients with antibodies to different VGKC Kv1-complex proteins. Control sera precipitate <100 pM (line)

Figure 12:
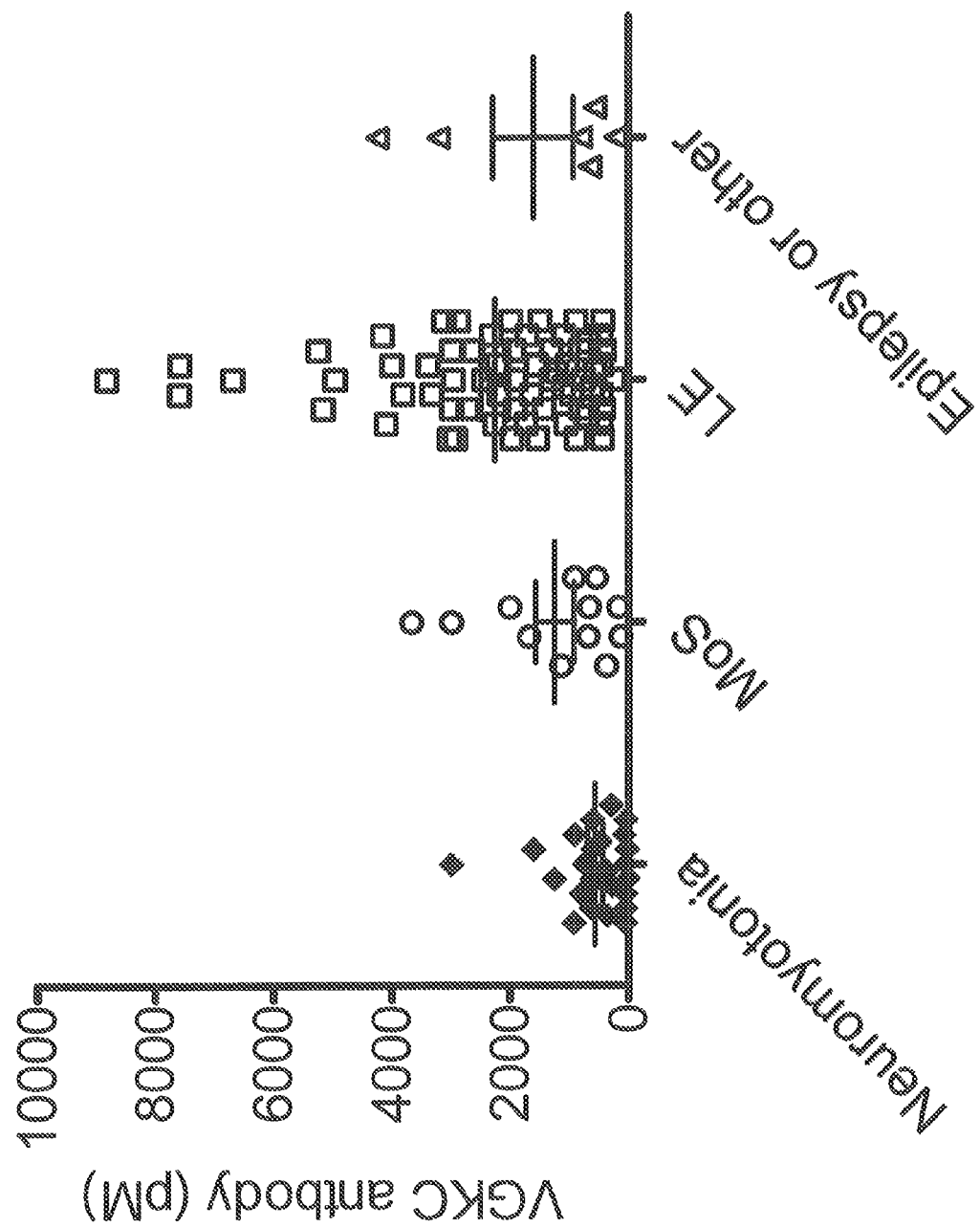

FIG. 12—VGKC antibody titres in the patients divided into different clinical phenotypes as determined from the questionnaires submitted by referring neurologists.

FIG. 13—is a table showing clinical features of 108 patients samples studied.

FIG. 14—is a table showing clinical features of patients as classified by antibody specificity. 36/39 patients with Lgi1 antibodies have limbic encephalitis, none have neuromyotonia, and none have thymic malignancies. By contrast, 10/27 patients with CASPR2 antibodies have Morvans' syndrome, 8 have neuromyotonia, and 10 have thymic malignancies. Thus recognition of these two distinct antibodies explains a large part of the clinical heterogeneity associated with "VGKC" antibodies.

RESULTS

LE/MoS Sera Immunoprecipitate $^{125}$I-αDTX-VGKCs from Rabbit Cortex Extracts but do not Inhibit VGKC Kv1.1 and 1.6 Currents LE/MoS sera are identified by their ability to immunoprecipitate $^{125}$I-αDTX-labelled VGKCs from a digitonin-extract of rabbit or human cortex, as illustrated for 8 sera (5 LE and 3 MoS) used in this study (FIG. 1a). Antibody titres were determined from these plots and varied between 2006 and 6412 pM (normal range <100 pM). To determine whether the antibodies bound to individual VGKCs, we expressed individual Kv1.1, 1.2 and 1.6 subunits in HEK cells. We first confirmed that there was expression of the appropriate subunits using indirect immunocytochemistry with rabbit anti-Kv1 antisera. Since these rabbit antibodies bind to intracellular epitopes, we permeabilised the cells. The antibodies showed specificity for their appropriate Kv1 subtype (FIG. 1b). Moreover, the cells expressed some of the Kv1 subunits on their surface as shown by Kv1.1 extracellular immunostaining (FIG. 1c) and by measurement of $^{125}$I-αDTX binding sites on unpermeabilised cells. Nevertheless, disappointingly, none of the 21 LE/MoS sera that we tested showed similarly detectable surface binding (FIG. 1c).

It was still a possibility that the sera would have an effect on the function or expression of the Kv1s. The transfected HEK cells demonstrated voltage-dependent currents that were inhibited by αDTX (FIG. 2a,b). We incubated the HEK cells expressing Kv1.1 or 1.6 in sera (diluted 1:50-1:1000) and compared the currents before and after the serum application (FIG. 2c,d). Healthy serum did not alter Kv1 currents when compared with medium alone. Although there was some variability in the mean currents recorded, overall there was no significant effect of the patient sera on the currents when compared with incubations in healthy control sera (one way ANOVA; FIG. 2c,d).

Some antibodies do not directly affect the function of their target antigens, but cause a time and temperature dependent increase in internalisation with a reduction in surface expression [12, 13]. To see if the patients' antibodies reduced cell surface expression over time, we incubated the cells for 1 or 3 days at 37° C. before testing the αDTX-sensitive currents [12]. However, there was no effect on the αDTX-sensitive currents (FIG. 3a-d). Thus overall, these results confirmed the presence of functional, αDTX-binding Kv1s on the HEK cell surface but could not demonstrate that the patients' antibodies bound to the cells or affected the function or numbers of the channels.

LE/MoS Sera do not Precipitate a Subpopulation of $^{125}$I-αDTX-VGKCs from Brain Extract and do not Precipitate $^{125}$I-αDTX-VGKCs from Kv-Transfected HEK Cells To investigate further, we compared the immunoprecipitation of $^{125}$I-αDTX-labelled VGKC extracted from rabbit cortex by patient sera with that by rabbit antibodies to Kv1.1, 1.2, and 1.6. All mammalian brain $^{125}$I-αDTX binding sites are thought to contain Kv1.2 [14]. Anti-Kv1.2 immunoprecipitated 81% of the 50,000 maximum $^{125}$I-αDTX binding sites (FIG. 4a). Further precipitation was not achieved with Kv1.1 or Kv1.6 antibody addition (supplementary data FIG. 1B). Hence, only 19% of $^{125}$I-αDTX is unbound to VGKCs. In contrast, precipitation by anti-Kv1.1, 1.6 and 1.4 plateaued at 51%, 17% and 7% respectively (FIG. 4a). These data are consistent with previously unpublished work using alternative Kv1 antibodies (supplementary data 1c). When we tested the individual LE/MoS sera in the same assay, however, they consistently immunoprecipitated less than the maximum counts of $^{125}$I-αDTX even at serum excess (FIG. 4a). Although the plateau values were not identical for each serum (FIG. 1a), the mean value was 32% (range 23-43%) of the maximum for all the LE/MoS sera tested (FIG. 4b).

These data suggest that the sera might be binding to subpopulations of αDTX-labelled channels. To explore further, we expressed Kv1.1, 1.2, 1.4, 1.6 and β2 subunits, both individually and together in HEK cells, and extracted the cells in 2% digitonin, in a manner identical to that used for the preparation of the rabbit cortex extract. The extract was $^{125}$I-αDTX labelled and tested for immunoprecipitation by the anti-Kv1s and the LE/MoS sera. The results of the individual rabbit antibodies were similar to those found with the rabbit cortex extract but there was no precipitation by the LE/MoS sera (FIG. 4c). Thus these results led us to conclude that the LE/MoS antibodies do not bind directly to either homomeric or heteromeric Kv1 subunits.

LE/MoS Bind to a Kv1-Complexed Protein.

One explanation for these findings was that the LE/MoS antibodies bind to a protein that is associated with the Kv1s in the rabbit cortex extracts but not present in the transfected HEK cells. To test this hypothesis, we treated the $^{125}$I-αDTX-labelled rabbit cortex extract with increasing concentrations of sodium dodecyl sulphate (SDS) and performed immunoprecipitations with rabbit anti-Kv1 antibodies and the LE/MoS sera. The results demonstrated a dissociation between the binding of the patients' antibodies and of the Kv1.1 and 1.2 antibodies to the αDTX-bound complexes (FIG. 5a), with the former being much more sensitive to the SDS treatment.

There are several proteins that have previously been reported to associate with Kv1s or DTX binding sites in brain extracts, including leucine-rich glioma inactivated gene 1 (Lgi1), contactin associated protein 2 (CASPR2), transient axonal glycoprotein-1 (TAG1) and post-synaptic density (PSD) members [9, 10, 15]. When we tested antibodies against these proteins, anti-Lgi1 immunoprecipitated 61% of the αDTX binding sites and TAG1 immunoprecipitated around 5%. However, anti-CASPR2 antibodies demonstrated reactivity very similar to that of the LE/MoS sera both in the proportion of αDTX-binding sites precipitated from the rabbit extract (FIG. 5b) and in the sensitivity to increasing concentrations of SDS (FIG. 5c). These findings indicate that a significant proportion of the αDTX-labelled VGKCs in our rabbit cortex extract are associated with CASPR2, and suggest that the LE/MoS antibodies may be binding directly to CASPR2. Similarly precipitation by Lgi1 antibodies demonstrated SDS sensitivity greater than that of the Kv1 specific antibodies (FIG. 5c), suggesting that this protein is also a potential target for LE/MoS antibodies.

Some LE/MoS Serum Antibodies Bind to CASPR2

To ask directly whether LE/MoS antibodies bound CASPR2, we expressed full-length human CASPR2 in HEK cells, after tagging the protein by introducing EGFP at the intracellular C-terminus. Many LE/MoS sera bound to the surface of these cells and not to the surface of cells transfected with the vector only (FIG. 6a). The advantage of using EGFP-tagged CASPR2 is that it can provide a rapid method to measure serum antibodies quantitatively in solution (as in Waters et al, for aquaporin-4 antibodies [16]). We tested 188 sera, which precipitate more than control values of $^{125}$I-αDTX-labelled rabbit cortex extract, for their ability to immunoprecipitate EGFP-CASPR2 by measuring the green fluorescence in the precipitates (FIG. 6b). Serum from healthy individuals or those with other neurological diseases did not precipitate appreciable fluorescence, and a value of 10 FUs was established as a cut-off. Overall 18% of the LE/MoS sera were positive with values varying between 12 and 100 FUs precipitated by each serum. These sera all bound to the extracellular domain of CASPR2 (FIG. 6a). Within the population of patients who were positive for this antibody, there was a very close correlation between binding to VGKCs in rabbit cortex extracts and direct binding to CASPR2 (FIG. 6c). To confirm further the specificity of the antibodies, we preabsorbed the sera with CASPR2-expressing HEK cells. This abolished immunoprecipitation of CASPR2 from CASPR2-EGFP extracts, and also abolished immunoprecipitation of $^{125}$I-αDTX-VGKCs from the rabbit cortex extract (FIG. 6d).

Characteristics of the Anti-CASPR2 Antibodies.

Many pathogenic autoantibodies are high affinity, IgG, complement-activating and conformation-dependent. Immunostaining of CASPR2-EGFP-expressing HEK cells with isotype-specific secondary antibodies allowed determination of the relative abundance of CASPR2 IgG subclasses (FIG. 7a). Most CASPR2 antibodies were of IgG1 and IgG4 subclasses with little IgG2 and almost no IgG3. We also tested limiting amounts of individual patients' sera for binding to different concentrations of CASPR2-EGFP and analysed the results by Scatchard plots. Five patients were analysed giving a mean Kd of $1.2+/-0.54\times10^{-8}$ (SD; FIG. 7b). Using western blotting, a commercial anti-CASPR2 antibody identified a strong band at 180 kDa in the CASPR2-transfected cell extracts but the ten CASPR2 antibody positive patients tested did not bind to this band suggesting that the CASPR2 antibodies bind to conformation epitopes that are not presented in denatured CASPR2 extracts (FIG. 7c).

A Few VGKC Antibody Positive Sera Bind to TAG1

We did not initially test many sera for binding to TAG1 because the anti-TAG1 antibodies only immunoprecipitated <10% of the 125I-αDTX binding sites from brain extracts (FIG. 5B). FIG. 8A shows that TAG1-transfected HEK cells have TAG1 on their surface as demonstrated by binding of a rabbit anti-TAG1. Binding of IgG from two patient's sera is shown in FIG. 8B. The sera bind to the extracellular surface of unpermeabilised TAG1 transfected (EGFP co-transfected) cells. We found TAG1 binding antibodies in four sera of the 108 tested.

A High Proportion of LE/MoS Sera Bind to Lgi1.

We found binding of serum IgG to Lgi1 transfected cells in a high proportion of sera (see below). However, the binding was not only to the surface of EGFP co-transfected HEK cells (EGFP positive, FIG. 9A), but also detected around cells that were not transfected (FIG. 9B). It appeared possible that the Lgi1 was secreted into the medium and then bound to the surface of all of the HEK cells, as this had been reported previously [24, 25 as above].

To see if this was the case, we took the supernatant from Lgi1-transfected cells and incubated it with untransfected HEK cells for 1 hour at room temperature. These non-transfected cells were then tested for bound Lgi1 by looking for binding of IgG from the sera with Lgi1 reactivity (ie as in FIG. 9A). The supernatant from Lgi1-transfected HEK cells (FIG. 10A), but not from cells expressing other antigens, eg. MuSK (FIG. 10B), was able to transfer Lgi1 to the surface of the HEK cells where it was bound by the Lgi1-positive patients' serum IgG. This confirms and extends a previous observation that Lgi1 is secreted and can attach to the cell surface of PC12 cells in culture (eg. [24, 25]).

Clinical Correlates of CASPR2, TAG1 and Lgi1 Antibodies

To establish the clinical relevance of our findings, we tested 108 sera from patients with VGKC antibodies for binding to HEK cells expressing the three antigens. These samples included 88 sera sent for routine analysis with high VGKC antibodies (>400 pM) which were expected to include mainly patients with CNS (LE or Morvans) disease, and an additional 20 sera (13 from patients with neuromyotonia and 7 from Morvan's syndrome). These were selected from our archives because Morvan's syndrome is rare, and because neuromyotonia patients typically have low levels of antibodies binding to $^{125}$I-αDTX-VGKCs and would have been under-represented in the high titre patients.

The VGKC antibody titres associated with the three different antibodies are shown in FIG. 11. This shows that the titres are highest in the Lgi1 positive patients, moderate in the CASPR2 positive patients and low in the TAG1 positive patients, including one serum that was <100 pM by immunoprecipitation of $^{125}$I-αDTX-VGKC.

We obtained clinical information from the referring neurologists, mainly from detailed questionnaires (Oxford Research Ethics Committee A approval, 07/Q160X/28). 65 of the patients had limbic encephalitis (six of whom had epilepsy as a major feature), 12 had Morvan's syndrome, 25 had neuromyotonia and only six had epilepsy, dystonia or startle syndromes that did not directly fit into those classifications. These patients represent well the known spectrum of disorders associated with VGKC antibodies. The distribution of VGKC antibody titres of the different patient clinical subgroups are shown in FIG. 12. As expected from previous data on individual patients, they were highest in limbic encephalitis, lower in Morvan's syndrome and lowest in neuromyotonia. The latter group included eight who were negative for VGKC antibodies on routine testing. FIG. 13 shows the clinical syndromes, the numbers of patients in each group, the numbers with evidence of non-thymic tumours (these were variable, and only two were clinically active at the time of sample referral) and the numbers with thymic malignancies, which are the only tumour type frequently associated with VGKC antibodies [5].

FIG. 14 shows the patients associated with each of the three different antibodies. Strikingly, Lgi1 antibodies were almost exclusively found in patients with limbic encephalitis—only three of the 39 Lgi1 positive sera were from patients with other syndromes—and importantly were not found in patients with thymic malignancies. By contrast, CASPR2 antibodies were found in the 10 of the 12 patients with Morvans syndrome and in 10/11 of the patients with thymic malignancies. In addition, CASPR2 antibodies were also found in 8 of the 25 patients with neuromyotonia. TAG1 antibodies were only found in four patients, but three of these had neuromyotonia, one of whom was negative for VGKC antibodies; the other TAG1 positive patient had limbic encephalitis.

Discussion

We describe CASPR2 as a novel autoantibody target in patients previously believed to have antibodies directed against central nervous system expressed Kv1-type potassium channels. In addition, we show that a high proportion of other patients had Lgi1 antibodies and a few had TAG1 antibodies including one patient who was negative on testing for VGKC antibodies. The presence of these antibodies correlates with different clinical features of the patients and, for the first time, these results demonstrate that the different clinical phenotypes are likely to depend on the presence of specific antibodies that target different VGKC Kv1-complex proteins in the nervous system. The antibodies that we define here represent 65% of the VGKC antibody positive samples. Further improvements in the antibody detection assays may increase this percentage.

αDTX labels Kv1.1, 1.2 and 1.6, the most abundant Kv1 subunits in mammalian brain. The observation that LE and MoS IgG immunoprecipitate αDTX-labelled brain proteins has been assumed to indicate direct binding of LE and MoS IgG to Kv1 proteins. Brain tissue immunohistochemistry has supported this hypothesis by showing co-localisation of Kv1.2, in particular, with patient sera [4], [3], [17]. Furthermore, one study has shown binding of LE and MoS IgG to Kv1s expressed in a heterologous mammalian cell line [8]. However, the 'preference' of LE or MoS sera for a particular Kv1 subtype fails to explain why patients with peripherally-generated anti-Kv1 antibodies can only display a central nervous system phenotype.

Functionally, passive transfer of IgG from patients with NMT creates electrophysiological changes consistent with neuronal hyperexcitability secondary to potassium channel dysfunction [1]. Similarly, patients with LE and MoS show features of neuronal hyperexcitability such as seizures, neuromyotonia and neuronal loss [2], [18] and patients with Kv1.1 mutations and Kv1.1-knockout mice develop seizures [19], [20]. These pieces of evidence have made Kv1 subunits the likeliest antigenic targets of LE and MoS IgG. However, no approach at the molecular level has convincingly confirmed this hypothesis.

If the LE or MoS IgG bound Kv1.1, they would be expected to precipitate the same amount of $^{125}$I-αDTX as an anti-Kv1.1 antibody. Although our data for anti-Kv1.1, 1.2, 1.4 and 1.6 precipitations are very similar to previous studies [14, 21], LE and MoS IgG precipitate a subpopulation of the Kv1s, not a similar amount to any single anti-Kv1 antibody. This suggests they do not bind any one of the Kv1 proteins.

Kv1 tetramerise to form functional, αDTX-sensitive channels on the surface of HEK cells. However, neither could we detect current suppression nor surface immunofluorescence-determined binding after exposure to LE and MoS IgG. To exclude the possibility that the IgG binds the intracellular domain of Kv1s, we solubilised cells under conditions intended to mimic the diagnostic assay and extract heteromers of the Kv1 subunits similar to those present in our brain tissue. Using this paradigm, we were unable to demonstrate LE or MoS IgG which precipitated $^{125}$I-αDTX-labelled Kv1s. Thus, although Kv1 dysfunction may be the molecular correlate of the LE and MoS phenotypes, and LE and MoS IgG precipitate counts from $^{125}$I-αDTX labelled mammalian brain homogenate, they do not do so by directly binding the Kv1 proteins. Therefore, it is likely they are coprecipitating another protein complexed to Kv1 in brain tissue, which is not present in Kv1-expressing HEK cells. This hypothesis was strengthened by the differential SDS sensitivities of Kv1.1/1.2 and LE/MoS antigens and specifically provided evidence for them binding to a separate, more peripheral, protein within $^{125}$I-αDTX-bound brain complexes.

CASPR2 is a Kv1-coprecipitating molecule with a large extracellular domain [9]. In addition, the dissociation pattern of CASPR2 from the αDTX complexes was similar to that of the LE and MoS patients. A FIPA using solubilised CASPR2-EGFP produced positive values in 32 (18%) of the diagnostic assay-positive patients. Anti-CASPR2 antibodies were absent in patients with central nervous system diseases, autonomic dysfunction or thymomas, who were negative in the diagnostic assay in the sera studied. All anti-CASPR2 IgG bound an epitope within the extracellular domain of CASPR2. These IgGs did not recognise linearised CASPR2 in western blots, suggesting they bind a conformational epitope available in mammalian expressed CASPR2. The anti-CASPR2 antibodies were predominantly of the IgG1 and 4 subclasses. The IgG1 subclass suggests a possible role for complement fixation in the pathogenesis of anti-CASPR2 antibody-associated diseases. These antibodies were of high affinity, similar to those found in other neurological diseases. The absence of detectable antibodies in the diagnostic assay after CASPR2 antibody immunoabsorption and the linear association between anti-CASPR2 titres and diagnostic assay titres strongly suggests these anti-CASPR2 are some of the antibodies previously referred to as voltage-gated potassium channel antibodies.

The solely neural expression of CASPR2 ensures an antibody-mediated pathology only occurs at the surface of neurons. This is consistent with the observed clinical features in LE and MoS patients. CASPR2 and Tag1 knockout mice show a diffuse Kv1 distribution throughout their axons, in contrast to the juxtaparanodal-clustered Kv1s seen in wild type neurons [22]. Similarly brain tissue from humans harbouring CASPR2 C-terminal truncations showed more diffuse Kv1 expression than seen in control brain. These patients developed seizures, cognitive impairment and absent tendon reflexes [23]. Given the central and peripheral nervous system distribution of CASPR2, this genetic model is analogous to our finding of MoS overrepresentation within anti-CASPR2 positive patients.

Anti-CASPR2 antibodies may produce similar dispersion of the previously clustered Kv1s, by three major mechanisms: i) complement fixation and focal tissue damage, ii) direct stimulation or block of their target protein and iii) internalisation of the target antigen. It is most likely that anti-CASPR2 antibodies mediate their action via 1) and iii). The reduced number of Kv1s may create a relatively depolarised, hyperexcitable membrane.

Similar considerations apply to the antibodies directed against Lgi1 or TAG1. Lgi1 is expressed principally in the central nervous system, and of particular interest in regions which do not express CASPR2, such as the mossy fibre layer of the hippocampus; this may explain why the patients with these antibodies predominantly display limbic encephalitis which is associated with temporal lobe MRI high signal and temporal lobe epilepsy [2]. Moreover, mutations in the gene encoding lgi1 are found in families with lateral temporal lobe epilepsy [28] who do not show any peripheral nerve dysfunction. By contrast TAG1 is expressed with Kv1.1 and Kv1.2 and CASPR2 at the nodes of Ranvier where it could provide a target for antibodies in patients with neuromyotonia and Tag1 knockout mice demonstrate dispersion of previously clustered Kv1 proteins at CNS and PNS juxtaparanodes [22, 27]. Altogether these findings provide a major new understanding of the clinical heterogeneity associated with anti-"VGKC" antibodies and will provide for much more precise identification and classification of patients in the future. The cell-based assays that we use here are frequently more sensitive than assays that depend on immunoprecipitation of the tagged antigen from solution (eg [11, 16]). For instance, in an additional cohort of 14 patients with neuromyotonia, we found CASPR2 or TAG1 antibodies in 5 who were negative for VGKC antibodies by the immunoprecipitation assay. Thus the identification of these targets, and the development of the assays, should not only explain the phenotypic differences but improve the diagnosis.

Methods

Clinical Material

Serum samples have been stored at −20° C. Clinicians provided clinical details to subclassify patients. LE sera were classified as those with amnesia and seizures without neuromyotonia. MoS sera had central nervous system features plus autonomic features and neuromyotonia. Controls included patients with thymomas (n=9), subacute-onset autonomic disease (n=34), multiple sclerosis (n=14), non-$I^{125}$-αDTX precipitating encephalopathies (n=50) and healthy controls (n=10). 88 sera were selected from sera with moderate to high VGKC antibody titres (all >400 pM), regardless of any known clinical phenotype. To obtain detailed clinical information, questionnaires were sent to the referring neurologists and the information collated in a database (Oxford Research Ethics Committee A approval, 07/Q160X/28). This enabled us to distinguish the three main clinical phenotypes. Six of the patients did not fit well into these categories: four had epilepsy only, one had dystonia with excessive startle, and one had excessive startle only. 20 additional sera from patients with known Morvan's syndrome (n=7) or neuromyotonia (n=13) were added in order to increase the number of these patients for confirmation of the findings and the statistical analyses.

Radioimmunoprecipitation of VGKCs Extracted from Rabbit Cortex

VGKC complexes were extracted from rabbit cortical membranes solubilised using 2% digitonin (Calbiochem, USA) in DTX-buffer (100 mM NaCl, 20 mM Tris, 5 mM KCl adjusted to pH 7.12) at 37° C. for 20 minutes. Supernatants were diluted 1:2 with PTX (0.02M phosphate buffer and 0.1% Triton X100) and incubated with $I^{125}$-αDTX (Perkin Elmer, USA). This extract was diluted with PTX to 1 million counts per minute (cpm) per ml. For dissociation experiments, sodium dodecyl sulfate (SDS) was added to the $I^{125}$-αDTX labelled extract for 2 hours at RT. 50 ul of $I^{125}$-αDTX-labelled extract was incubated with serum or commercial antibodies (made up to 50 ul with PTX) overnight at 4° C. Secondary antibodies (anti-human IgG (The Binding Site, UK) or anti-goat IgG (Jackson Immunoresearch Laboratories Inc, USA)) were added at 10 ul/1 ul serum for 90 minutes at RT. Precipitates were spun in 0.5 ml PTX and resulting pellets washed twice in PTX and read on a gamma counter (Cobra2, Perkin Elmer). When expressed as specific cpm, results have healthy control data subtracted.

Plasmid Constructs cDNAs encoding full-length human Kv1.1, 1.2, 1.4, 1.6 and β2 were cloned into pcDNA3.1-hygro (Invitrogen Ltd, CA, USA). The full-length human MuSK-GFP construct has been described previously [2]. The vector pCR4-TOPO that contained the cDNA for CASPR2 (IMAGE: 7939625 from geneservice, Cambridge, England) was digested with EcoRI. The fragment was subcloned into pcDNA3.1 (+) (Invitrogen, UK) to give an untagged CASPR2 that expressed in mammalian cells. In order to tag CASPR2 with EGFP, the pcDNA3.1 (+)-CASPR2 plasmid was digested with XhoI and XmaI. The fragment was subcloned into pEGFP-N1 (Clontech Laboratories, CA, USA).

For human Lgi-1, the cDNA was bought from Geneservice Ltd. and amplified by PCR with the following primers:

(SEQ ID NO: 1)
FPlgi1pcdna:
GATCGCTAGCCCACCATGGAATCAGAAAGAAGCAAAAGG
NheI (SEQ ID NO: 2)
RPlgi1pcdna:
GATCCTCGAGTCATGCGCTTAAGTCAACTATGACATG
XhoI The purified product was subcloned into pGEM-Teasy. This clone and the plasmid pcDNA3.1(+) from Clontech were digested with NheI and XhoI. The fragments were ligated together; the construct was purified and verified by sequencing.

(SEQ ID NO: 1)
FPlgi1pcdna:
GATCGCTAGCCCACCATGGAATCAGAAAGAAGCAAAAGG
NheI (SEQ ID NO: 2)
RPlgi1pcdna:
GATCCTCGAGTCATGCGCTTAAGTCAACTATGACATG
XhoI Human TAG1 cDNA was obtained as a gift from Dr D Karagogeos (University of Crete; see [27])

Transfection and Human Embryonic Kidney Cell Culture

HEK293 cells were cultured in Dulbecco's modified eagle's medium (DMEM) supplemented with 10% foetal calf serum (FCS, TCS Cellworks Ltd, Buckingham, UK) and 100 units/ml each of penicillin G and streptomycin (Invitrogen, CA, USA) at 37° C. in a 5% $CO_2$ atmosphere. Cells were grown on 6 well culture plates for immunoabsorption and toxin binding experiments, on 13 mm glass coverslips placed in 6-well cell culture plates for microscopy and on 175 $cm^2$ flasks for protein extraction. Using polyethylenimine (PEI), cells were transiently co-transfected with Kv1.1, 1.2, 1.4, 1.6, β2, EGFP (enhanced green fluorescence protein), MuSK-EGFP, CASPR2-EGFP, Lgi1 or TAG1 cDNA The expression of EGFP was visualised using an Axion 200 inverted Zeiss fluorescence microscope.

Immunocytochemistry 48 hours post-transfection immunofluorescent staining of HEK cells was performed. Coverslips were transferred to 24-well culture plates and incubated with mouse anti-Kv1.1 extracellular domain antibody (1:100, a gift from Dr J Trimmer, California) or patient sera (1:20-100) diluted in DMEM-N-(2-hydroxyethyl)piperazine-N'-(2-ethanesulphonic acid) (HEPES) with 1% bovine serum albumin (BSA) at room temperature (RT) for 1 hour. Cells were subsequently washed 3 times in DMEM-HEPES buffer and fixed with 3% formaldehyde in phosphate buffered saline (PBS) at RT for 15 minutes. Cells were washed as above and labelled for 45 minutes at RT with: (i) anti-mouse IgG or anti-human IgG Alexa Fluor 568-conjugated secondary antibody (Invitrogen-Molecular probes, Paisley, UK) at 1:750 in 1% BSA-DMEM-HEPES buffer or (ii) mouse anti-human IgG1, 2, 3 or 4 (Binding Site, Birmingham, UK) at 1:50 in 1% BSA-DMEM-HEPES buffer and subsequently goat anti-mouse isotype specific IgG-Alexa Fluor 568-conjugated antibody (Invitrogen-Molecular probes, Paisley, UK). For cell permeabilisation, cells were initially incubated with fixative (as above) and subsequently all solutions contained 0.1% TritonX100. Rabbit anti-Kv1.1/ 1.2 and 1.6 antibodies (1:500, Alamone, Israel) were visualised with an anti-rabbit IgG Alexa Fluor 568-conjugated secondary antibody (Invitrogen-Molecular probes, Paisley, UK). Cells were subsequently washed 3 times in PBS and mounted on slides in fluorescent mounting medium (DakoCytomation, Cambridge, UK) with DAPI (4',6'-diamidino-2-phenlindoledichloride, 1:1000). They were visualised using a fluorescence microscope with a MacProbe v4.3 digital imaging system. For subclass analysis, all slides were examined by 3 blinded observers using a 0 to 4 scoring system as previously validated [11]. For TAG1 and Lgi1 we used mouse anti TAG1 (IgG1) purchased from developmental studies hybridoma bank for academic purposes ('3.1C12' from http://dshb.biology.uiowa.edu/), and goat anti Lgi1, C19 (sc-9583) and N18 (sc-9581) purchased from Santa Cruz Biotechnology Inc.

Electrophysiology

HEK-293 cells were transfected with Kv1.1 and GFP or Kv1.6 and GFP (as above) and plated directly onto glass coverslips for whole-cell patch clamp recordings. Voltage clamp recordings of cells were made in a stationary bath (1 ml volume) of external buffer containing (in mM): 145 NaCl, 6 KCl, 1 $MgCl_2$, HEPES, 2 $CaCl_2$, and 5 glucose; pH 7.4 with NaOH. Recording pipettes of ~2-5MΩ resistance were prepared from borosilicate capillary glass (Harvard Apparatus), and filled with standard intracellular solution containing (in mM): 150 KCl, 10 EGTA, 1 $CaCl_2$, 1 $MgCl_2$ and 10 HEPES; pH 7.4 with KOH. Cells were visualised using an inverted fluorescent microscope (Nikon) and only GFP-expressing cells were recorded. Recordings were made at room temperature (20-24° C.). Preliminary experiments, using CsCl-based intracellular solution, confirmed that the currents shown are potassium mediated (data not shown).

α-DTX-sensitive currents were demonstrated by direct bath application of α-DTX (1 μM, Sigma-Aldrich) during recordings; an equivalent volume of buffer solution was used in control experiments. Serum samples were dialysed against the external recording solution prior to use and samples to be applied chronically were diluted in culture medium (1:50-1:1000). Acute effects of sera on expressed currents were determined by direct serum application during recording, analogous to the addition of α-DTX. Chronic effects of patient sera were determined by 1-3 day incubation with Kv1-transfected HEK-293 cells at 37° C. prior to recording.

Data were low-pass filtered at 1 kHz and acquired at 10 kHz. Recordings were made using an Axopatch-1D amplifier, a Digidata 1320 series digitizer and the pClamp suite of programs for pulse generation, data acquisition and data analysis (Axon Instruments). Cells included in analysis had low access resistances (Ra, <20 MΩ) with less than 30% change during the recording; high input resistances (Ri, >1GΩ at −70 mV (+10 mV step); baseline stability and small leak current (<−50 pA). Peak current measurements were made by applying a 300 ms test pulse at +40 mV from a holding potential of −80 mV. Voltage-dependence of activation and steady-state inactivation were also analysed (data not shown). Statistical significances were assessed using two-tailed Student t-tests for single comparisons and one-way ANOVAs for multiple comparisons.

Protein Extraction and Labelling

At 48 hours post-transfection, confluent 175 $cm^2$ flasks were washed with PBS and lysed in 2% digitonin in DTX-buffer, with 1:100 protease inhibitor cocktail (Sigma-Aldrich, UK). Lysates were rotated for 1 hour, spun (13,000 rpm for 5 minutes at 4° C.) and labelled with $I^{125}$-αDTX as above. Both these and GFP-tagged extracts (100 fU/assay) were subject to immunoprecipitation with 5 ul of human sera or a rabbit anti-CASPR2 (gift from Dr E Peles) antibody. Pellets were resuspended in 180 ul PTX, transferred to a 96 well plate and analysed using a fluorescent plate reader (Gemini XS, Molecular Probes). This latter assay is known as a fluorescent immunoprecipitation assay (FIPA).

Western Blotting

Transfected cell extracts were boiled with SDS-based loading buffer and reducing agent (Invitrogen, CA, USA). 4-12% SDS polyacrylamide gels (Invitrogen, UK) were loaded with 15 ul of extract per well (equalised for protein concentrations) and run for 90 minutes at 200 mV. Gels were transferred to nitrocellulose paper over 90 minutes at 30 mV. Individual strips were blocked with a PBS-0.1% tween, 5% milk protein solution. Subsequently, membranes were incubated for 1 hour with primary antibodies diluted in blocking solution (1:100), PBS-0.1% tween for 3 washes and 30 minutes in HRP-conjugated anti-rabbit or anti-human IgG secondary antibodies (DakoCytomation, UK) diluted in blocking solution (1:200). Blots were developed with diaminobenzidine (DAB).

REFERENCES

[1] Sinha S, Newsom-Davis J, Mills K, Byrne N, Lang B, Vincent A. Autoimmune aetiology for acquired neuromyotonia (Isaacs' syndrome). Lancet. 1991 Jul. 13; 338(8759): 75-7.

[2] Vincent A, Buckley C, Schott J M, Baker I, Dewar B K, Detert N, Clover L, Parkinson A, Bien C G, Omer S, Lang B, Rossor M N, Palace J. Potassium channel antibody-associated encephalopathy: a potentially immunotherapy-responsive form of limbic encephalitis. Brain. 2004 March; 127 (Pt 3):701-12

[3] Buckley C, Oger J, Clover L, Tuzun E, Carpenter K, Jackson M, et al. Potassium channel antibodies in two patients with reversible limbic encephalitis. Ann Neurol. 2001 July; 50(1):73-8.

[4] Liguori R, Vincent A, Clover L, Avoni P, Plazzi G, Cortelli P, et al. Morvan's syndrome: peripheral and central nervous system and cardiac involvement with antibodies to voltage-gated potassium channels. Brain. 2001 December; 124 (Pt 12):2417-26.

[5] Hart I K, Waters C, Vincent A, Newland C, Beeson D, Pongs O, et al. Autoantibodies detected to expressed K+ channels are implicated in neuromyotonia. Annals of neurology. 1997 February; 41(2):238-46.

[6] Shillito P, Molenaar P C, Vincent A, Leys K, Zheng W, van den Berg R J, et al. Acquired neuromyotonia: evidence for autoantibodies directed against K+ channels of peripheral nerves. Annals of neurology. 1995 November; 38(5):714-22.

[7] Tomimitsu H, Arimura K, Nagado T, Watanabe O, Otsuka R, Kurono A, et al. Mechanism of action of voltage-gated K+ channel antibodies in acquired neuromyotonia. Annals of neurology. 2004 September; 56(3):440-4.

[8] Kleopa K A, Elman L B, Lang B, Vincent A, Scherer S S. Neuromyotonia and limbic encephalitis sera target mature Shaker-type K+ channels: subunit specificity correlates with clinical manifestations. Brain. 2006 June; 129 (Pt 6):1570-84.

[9] Poliak S, Gollan L, Martinez R, Custer A, Einheber S, Salzer J L, et al. Caspr2, a new member of the neurexin superfamily, is localized at the juxtaparanodes of myelinated axons and associates with K+ channels. Neuron. 1999 December; 24 (4):1037-47.

[10] Schulte U, Thumfart J O, Klocker N, Sailer C A, Bildl W, Biniossek M, et al. The epilepsy-linked Lgi1 protein assembles into presynaptic Kv1 channels and inhibits inactivation by Kvbeta1. Neuron. 2006 Mar. 2; 49(5):697-706.

[11] Leite M I, Jacob S, Viegas S, Cossins J, Clover L, Morgan B P, et al. IgG1 antibodies to acetylcholine receptors in 'seronegative' myasthenia gravis. Brain. 2008 May 31.

[12] Nagado T, Arimura K, Sonoda Y, Kurono A, Horikiri Y, Kameyama A, et al. Potassium current suppression in patients with peripheral nerve hyperexcitability. Brain. 1999 November; 122 (Pt 11):2057-66.

[13] Hinson S R, Pittock S J, Lucchinetti C F, Roemer S F, Fryer J P, Kryzer T J, et al. Pathogenic potential of IgG binding to water channel extracellular domain in neuromyelitis optica. Neurology. 2007 Dec. 11; 69(24):2221-31.

[14] Shamotienko O G, Parcej D N, Dolly J O. Subunit combinations defined for K+ channel Kv1 subtypes in synaptic membranes from bovine brain. Biochemistry. 1997 Jul. 8; 36(27):8195-201.

[15] Kim E, Niethammer M, Rothschild A, Jan Y N, Sheng M. Clustering of Shaker-type K+ channels by interaction with a family of membrane-associated guanylate kinases. Nature. 1995 Nov. 2; 378(6552):85-8.

[16] Waters P, Jarius S, Littleton E, Leite M I, Jacob S, Gray B, et al. Aquaporin-4 antibodies in neuromyelitis optica and longitudinally extensive transverse myelitis. Archives of Neurology. 2008 July; 65(7):913-9.

[17] Ances B M, Vitaliani R, Taylor R A, Liebeskind D S, Voloschin A, Houghton D J, et al. Treatment-responsive limbic encephalitis identified by neuropil antibodies: MRI and PET correlates. Brain. 2005 August; 128 (Pt 8):1764-77.

[18] Schott J M, Harkness K, Barnes J, della Rocchetta A I, Vincent A, Rossor M N. Amnesia, cerebral atrophy, and autoimmunity. Lancet. 2003 Apr. 12; 361(9365):1266.

[19] Zuberi S M, Eunson L H, Spauschus A, De Silva R, Tolmie J, Wood N W, et al. A novel mutation in the human voltage-gated potassium channel gene (Kv1.1) associates with episodic ataxia type 1 and sometimes with partial epilepsy. Brain. 1999 May; 122 (Pt 5):817-25.

[20] Smart S L, Lopantsev V, Zhang C L, Robbins C A, Wang H, Chiu S Y, et al. Deletion of the K(V)1.1 potassium channel causes epilepsy in mice. Neuron. 1998 April; 20 (4):809-19.

[21] Scott V E, Muniz Z M, Sewing S, Lichtinghagen R, Parcej D N, Pongs O, et al. Antibodies specific for distinct Kv subunits unveil a heterooligomeric basis for subtypes of alpha-dendrotoxin-sensitive K+ channels in bovine brain. Biochemistry. 1994 Feb. 22; 33(7):1617-23.

[22] Poliak S, Salomon D, Elhanany H, Sabanay H, Kiernan B, Pevny L, et al. Juxtaparanodal clustering of Shaker-like K+ channels in myelinated axons depends on Caspr2 and TAG-1. The Journal of cell biology. 2003 Sep. 15; 162(6): 1149-60.

[23] Strauss K A, Puffenberger E G, Huentelman M J, Gottlieb S, Dobrin S E, Parod J M, et al. Recessive symptomatic focal epilepsy and mutant contactin-associated protein-like 2. The New England journal of medicine. 2006 Mar. 30; 354(13):1370-7.

[24] Sirerol-Piquer M S, Ayerdi-Izquierdo A, Morante-Redolat J M, Herranz-Pérez V, Favell K, Barker P A, Pérez-Tur J. The epilepsy gene LGI1 encodes a secreted glycoprotein that binds to the cell surface. Hum Mol Genet. 2006 Dec. 1; 15(23):3436-45. Epub 2006 Oct. 26.

[25] Fukata Y, Adesnik H, Iwanaga T, Bredt D S, Nicoll R A, Fukata M. Epilepsy-related ligand/receptor complex LGI1 and ADAM22 regulate synaptic transmission. Science. 2006 Sep. 22; 313(5794):1792-5.

[26] Pavlou O, Theodorakis K, Falk J, Kutsche M, Schachner M, Faivre-Sarrailh C, Karagogeos D Analysis of interactions of the adhesion molecule TAG-1 and its domains with other immunoglobulin superfamily members. Mol Cell Neurosci. 2002 July; 20(3):367-81.

[27] Traka M, Goutebroze L, Denisenko N, Bessa M, Nifli A, Havaki S, Iwakura Y, Fukamauchi F, Watanabe K, Soliven B, Girault J A, Karagogeos D. Association of TAG-1 with Caspr2 is essential for the molecular organization of juxtaparanodal regions of myelinated fibers. J Cell Biol. 2003 Sep. 15; 162(6):1161-72.

[28] Kalachikov S, Evgrafov O, Ross B, Winawer M, Barker-Cummings C, Martinelli Boneschi F, Choi C, Morozov P, Das K, Teplitskaya E, Yu A, Cayanis E, Penchaszadeh G, Kottmann A H, Pedley T A, Hauser W A, Ottman R, Gilliam T C. Mutations in LGI1 cause autosomal-dominant partial epilepsy with auditory features. Nat Genet. 2002 March; 30(3):335-41.

The invention claimed is:

1. A method of detecting the presence or absence of autoantibodies in a human comprising:
   obtaining a bodily fluid sample from the human;
   contacting the bodily fluid sample with an epitope of at least one Kv1-complex protein selected from contactin associated protein 2 (CASPR2), leucine-rich glioma inactivated gene 1 (Lgi1), and transient axonal glycoprotein-1 (TAG1); and
   detecting in the bodily fluid sample the presence or absence of at least one antibody-antigen complex formed between autoantibodies to an epitope of at least one Kv1-complex protein present in the bodily fluid sample and the epitope of the at least one Kv1-complex protein.

2. The method of claim 1, further comprising the step of assessing the clinical symptoms of the human, wherein the clinical symptoms comprise at least one of peripheral nerve hyperexcitability syndrome, muscle cramps, stiffness, pain, excessive sweating, constipation, cardiac irregularities, confusion, hallucinations, insomnia, amnesia, personality disorders, psychiatric disorders, seizures, epilepsy, thymic tumors, lung carcinoma, lymphoma, gynaecological malignancies, dystonia, and excessive startle.

3. The method of claim 1, wherein the bodily fluid is selected from the group comprising plasma, serum, whole blood, urine, sweat, lymph, feces, cerebrospinal fluid, and nipple aspirate.

4. The method of claim 1, wherein detecting in the bodily fluid sample the presence or absence of at least one antibody-antigen complex comprises the use of at least one immunoassay technique selected from enzyme-linked immunosorbent assay (ELISA), radioimmunoassay, immunoprecipitation, immunoagglutination, a competition assay, an inhibition assay, and a sandwich assay.

5. The method of claim 1, wherein detecting in the bodily fluid sample the presence or absence of at least one antibody-antigen complex comprises the use of a secondary antibody.

6. The method of claim 1, wherein the epitope of at least one Kv1-complex protein is an epitope of CASPR2.

7. The method of claim 1, wherein the epitope of at least one Kv1-complex protein is an epitope of Lgi1.

8. The method of claim 1, wherein the epitope of at least one Kv1-complex protein is an epitope of TAG1.

9. A method of detecting the presence or absence of autoantibodies in a human comprising:
obtaining a bodily fluid sample from the human;
contacting the bodily fluid sample with an epitope of at least one Kv1-complex protein selected from contactin associated protein 2 (CASPR2), leucine-rich glioma inactivated gene 1 (Lgi1), and transient axonal glycoprotein-1 (TAG1); and
detecting in the bodily fluid sample the presence or absence of at least one antibody-antigen complex formed between autoantibodies to an epitope of at least one Kv1-complex protein present in the bodily fluid sample and the epitope of the at least one Kv1-complex protein,
wherein the epitope of the at least one Kv1-complex protein is immobilized on a solid support.

10. The method of claim 9, further comprising quantitatively measuring the at least one antibody-antigen complex.

11. A method of aiding the diagnosis of an autoimmune neurological disorder in a human, the method comprising:
obtaining a bodily fluid sample from the human;
contacting the bodily fluid sample with an epitope of at least one Kv1-complex protein selected from contactin associated protein 2 (CASPR2), leucine-rich glioma inactivated gene 1 (Lgi1), and transient axonal glycoprotein-1 (TAG1); and
detecting in the bodily fluid sample the presence or absence of at least one antibody-antigen complex formed between autoantibodies to an epitope of at least one Kv1-complex protein present in the bodily fluid sample and the epitope of the at least one Kv1-complex protein.

12. The method of claim 11, wherein the autoimmune neurological disorder is selected from at least one of limbic encephalitis, Morvan's syndrome, and neuromyotonia.

13. The method of claim 11, wherein the epitope of at least one Kv1-complex protein is an epitope of CASPR2.

14. The method of claim 11, wherein the epitope of at least one Kv1-complex protein is an epitope of Lgi1.

15. The method of claim 11, wherein the epitope of at least one Kv1-complex protein is an epitope of TAG1.

16. The method of claim 11, further comprising assessing the clinical symptoms of the human.

17. The method of claim 16, wherein the clinical symptoms comprise at least one of peripheral nerve hyperexcitability syndrome, muscle cramps, stiffness, pain, excessive sweating, constipation, cardiac irregularities, confusion, hallucinations, insomnia, amnesia, personality disorders, psychiatric disorders, seizures, epilepsy, thymic tumors, lung carcinoma, lymphoma, gynaecological malignancies, dystonia, and excessive startle.

18. The method of claim 11, wherein the epitope of the at least one Kv1-complex protein is immobilized on a solid support.

19. A method of detecting the presence or absence of autoantibodies in a mammal comprising:
obtaining a bodily fluid sample from the mammal;
contacting the bodily fluid sample with an epitope of at least one Kv1-complex protein selected from contactin associated protein 2 (CASPR2), leucine-rich glioma inactivated gene 1 (Lgi1), and transient axonal glycoprotein-1 (TAG1); and
detecting in the bodily fluid sample the presence or absence of at least one antibody-antigen complex formed between autoantibodies to an epitope of at least one Kv1-complex protein present in the bodily fluid sample and the epitope of the at least one Kv1-complex protein,
wherein detecting in the bodily fluid sample the presence or absence of at least one antibody-antigen complex comprises the use of a tagged or labelled secondary antibody or a tagged or labelled epitope of the at least one Kv1-complex protein.

20. A method of aiding the diagnosis of an autoimmune neurological disorder in a mammal, the method comprising:
obtaining a bodily fluid sample from the mammal;
contacting the bodily fluid sample with an epitope of at least one Kv1-complex protein selected from contactin associated protein 2 (CASPR2), leucine-rich glioma inactivated gene 1 (Lgi1), and transient axonal glycoprotein-1 (TAG1); and
detecting in the bodily fluid sample the presence or absence of at least one antibody-antigen complex formed between autoantibodies to an epitope of at least one Kv1-complex protein present in the bodily fluid sample and the epitope of the at least one Kv1-complex protein,
wherein detecting in the bodily fluid sample the presence or absence of at least one antibody-antigen complex comprises the use of a tagged or labelled secondary antibody or a tagged or labelled epitope of the at least one Kv1-complex protein.

* * * * *